United States Patent
Furusato et al.

(10) Patent No.: US 10,144,871 B2
(45) Date of Patent: *Dec. 4, 2018

(54) LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Yoshimasa Furusato, Chiba (JP); Masayuki Saito, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/028,942

(22) PCT Filed: Sep. 25, 2014

(86) PCT No.: PCT/JP2014/075344
§ 371 (c)(1),
(2) Date: Apr. 13, 2016

(87) PCT Pub. No.: WO2015/056540
PCT Pub. Date: Apr. 23, 2015

(65) Prior Publication Data
US 2016/0257882 A1 Sep. 8, 2016

(30) Foreign Application Priority Data

Oct. 17, 2013 (JP) .................................. 2013-215978

(51) Int. Cl.
| | |
|---|---|
| C09K 19/30 | (2006.01) |
| C09K 19/34 | (2006.01) |
| C09K 19/20 | (2006.01) |
| C07C 43/225 | (2006.01) |
| C09K 19/02 | (2006.01) |
| G02F 1/1362 | (2006.01) |
| C09K 19/04 | (2006.01) |
| C09K 19/12 | (2006.01) |

(52) U.S. Cl.
CPC ........ *C09K 19/3402* (2013.01); *C07C 43/225* (2013.01); *C09K 19/0208* (2013.01); *C09K 19/0216* (2013.01); *C09K 19/20* (2013.01); *C09K 19/3066* (2013.01); *G02F 1/1362* (2013.01); *C09K 2019/0466* (2013.01); *C09K 2019/123* (2013.01); *C09K 2019/301* (2013.01); *C09K 2019/3004* (2013.01); *C09K 2019/3019* (2013.01); *C09K 2019/3021* (2013.01); *C09K 2019/3078* (2013.01); *C09K 2019/3083* (2013.01); *C09K 2019/3422* (2013.01)

(58) Field of Classification Search
CPC ...................................................... C09K 19/42
See application file for complete search history.

(56) References Cited

U.S. PATENT DOCUMENTS

| | | | |
|---|---|---|---|
| 2003/0222244 A1 | 12/2003 | Torii et al. | |
| 2011/0291048 A1* | 12/2011 | Hamano | C09K 19/20 252/299.61 |
| 2012/0241671 A1 | 9/2012 | Hattori et al. | |
| 2012/0313043 A1* | 12/2012 | Maeda | C09K 19/20 252/299.61 |
| 2014/0049743 A1* | 2/2014 | Furusato | C09K 19/08 349/186 |

FOREIGN PATENT DOCUMENTS

| | | |
|---|---|---|
| JP | 2002-327175 | 11/2002 |
| JP | 2003-301178 | 10/2003 |
| JP | 2003-301179 | 10/2003 |
| JP | 2013-001725 | 1/2013 |
| WO | 2011062049 | 5/2011 |
| WO | 2012163470 | 12/2012 |
| WO | WO 2012163470 A1 * 12/2012 | ......... C09K 19/0275 |

OTHER PUBLICATIONS

"International Search Report (Form PCT/ISA/210) of PCT/JP2014/075344", with English translation thereof, dated Oct. 28, 2014, pp. 1-4.

* cited by examiner

*Primary Examiner* — Chanceity N Robinson
(74) *Attorney, Agent, or Firm* — JCIPRNET

(57) ABSTRACT

To show a liquid crystal composition satisfying at least one of characteristics such as a high maximum temperature of a nematic phase, a low minimum temperature of the nematic phase, small viscosity, suitable optical anisotropy, large dielectric anisotropy, large specific resistance, high stability to ultraviolet light and heat; a liquid crystal composition having a suitable balance regarding at least two of the characteristics; and an AM device having a short response time, a large voltage holding ratio, a large contrast ratio, a long service life and so forth. The liquid crystal composition has the nematic phase and contains a specific compound having large dielectric anisotropy as a first component, and may contain a specific compound having a high maximum temperature or small viscosity as a second component, and a specific compound having large dielectric anisotropy as a third component, and a liquid crystal display device includes the composition.

10 Claims, No Drawings

LIQUID CRYSTAL COMPOSITION AND LIQUID CRYSTAL DISPLAY DEVICE

CROSS-REFERENCE TO RELATED APPLICATION

This application is a 371 application of an International PCT application serial no. PCT/JP2014/075344, filed on Sep. 25, 2014, which claims the priority benefits of Japan Application No. 2013-215978, filed on Oct. 17, 2013. The entirety of each of the above-mentioned patent applications is hereby incorporated by reference herein and made a part of this specification.

TECHNICAL FIELD

The invention relates to a liquid crystal composition, a liquid crystal display device including the composition, and so forth. In particular, the invention relates to a liquid crystal composition having a positive dielectric anisotropy, and an active matrix (AM) device including the composition and having a TN, OCB, IPS, FFS or FPA mode.

BACKGROUND ART

In a liquid crystal display device, a classification based on an operating mode for liquid crystal molecules includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode, a fringe field switching (FFS) mode and a field-induced photo-reactive alignment (FPA) mode. A classification based on a driving mode in the device includes a passive matrix (PM) and an active matrix (AM). The PM is classified into static, multiplex and so forth, and the AM is classified into a thin film transistor (TFT), a metal insulator metal (MIM) and so forth. The TFT is further classified into amorphous silicon and polycrystal silicon. The latter is classified into a high temperature type and a low temperature type according to a production process. A classification based on a light source includes a reflective type utilizing natural light, a transmissive type utilizing backlight and a transflective type utilizing both the natural light and the backlight.

The liquid crystal display device includes a liquid crystal composition having a nematic phase. The composition has suitable characteristics. An AM device having good characteristics can be obtained by improving the characteristics of the composition. Table 1 below summarizes a relationship of the characteristics between two aspects. The characteristics of the composition will be further described based on a commercially available AM device. A temperature range of the nematic phase relates to a temperature range in which the device can be used. A preferred maximum temperature of the nematic phase is about 70° C. or higher and a preferred minimum temperature of the nematic phase is about −10° C. or lower. Viscosity of the composition relates to a response time in the device. A short response time is preferred for displaying moving images on the device. A shorter response time even by one millisecond is desirable. Accordingly, a small viscosity in the composition is preferred. A small viscosity at a low temperature is further preferred. An elastic constant of the composition relates to contrast in the device. A larger elastic constant in the composition is further preferred in order to increase the contrast in the device.

TABLE 1

Characteristics of Composition and AM Device

| No. | Characteristics of Composition | Characteristics of AM Device |
|---|---|---|
| 1 | Wide temperature range of a nematic phase | Wide usable temperature range |
| 2 | Small viscosity[1] | Short response time |
| 3 | Suitable optical anisotropy | Large contrast ratio |
| 4 | Large positive or negative dielectric anisotropy | Low threshold voltage and small electric power consumption Large contrast ratio |
| 5 | Large specific resistance | Large voltage holding ratio and large contrast ratio |
| 6 | High stability to ultraviolet light and heat | Long service life |
| 7 | Large elastic constant | Large contrast ratio, short response time |

[1] A composition can be injected into a liquid crystal display device in a shorter period of time.

An optical anisotropy of the composition relates to the contrast ratio in the device. According to a mode of the device, a large optical anisotropy or a small optical anisotropy, namely a suitable optical anisotropy is required. A product ($\Delta n \times d$) of the optical anisotropy ($\Delta n$) of the composition and a cell gap (d) in the device is designed so as to maximize the contrast ratio. A suitable value of the product depends on a type of the operating mode. In a device having the mode such as TN, a suitable value is about 0.45 micrometer. In the above case, a composition having a large optical anisotropy is preferred for a device having a small cell gap. A large dielectric anisotropy in the composition contributes to a low threshold voltage, a small power consumption and a large contrast ratio in the device. Therefore, a large dielectric anisotropy is preferred. A large specific resistance in the composition contributes to a large voltage holding ratio and a large contrast ratio in the device. Accordingly, a composition having a large specific resistance at room temperature and also at a temperature close to a maximum temperature of the nematic phase in an initial stage is preferred. A composition having a large specific resistance at room temperature and also at a temperature close to a maximum temperature of the nematic phase after the device has been used for a long period of time is preferred. Stability of the composition to ultraviolet light and heat relates to a service life of the liquid crystal display device. In the case where the stability is high, the device has a long service life. Such characteristics are preferred for an AM device used in a liquid crystal projector, a liquid crystal television and so forth.

A composition having a positive dielectric anisotropy is used for an AM device having the TN mode. A composition having a negative dielectric anisotropy is used for an AM device having the VA mode. A composition having a positive or negative dielectric anisotropy is used for an AM device having the IPS mode or the FFS mode. A composition having a positive or negative dielectric anisotropy is used for an AM device having the polymer sustained alignment (PSA) mode. Examples of the liquid crystal composition having the positive dielectric anisotropy are disclosed in Patent literature No. 1 as described below.

CITATION LIST

Patent Literature

Patent literature No. 1: WO 2011-062049 A.

SUMMARY OF INVENTION

Technical Problem

One of the aims of the invention is to provide a liquid crystal composition satisfying at least one of characteristics such as a high maximum temperature of a nematic phase, a low minimum temperature of the nematic phase, a small viscosity, a suitable optical anisotropy, a large dielectric anisotropy, a large specific resistance, a high stability to ultraviolet light, a high stability to heat and a large elastic constant. Another aim is to provide a liquid crystal composition having a suitable balance regarding at least two of the characteristics. A further aim is to provide a liquid crystal display device including such a composition. An additional aim is to provide an AM device having a short response time, a large voltage holding ratio, a low threshold voltage, a large contrast ratio, a large contrast ratio, a long service life and so forth.

Solution to Problem

The invention concerns a liquid crystal composition that has a nematic phase and contains at least one compound selected from the group of compounds represented by formula (1) as a first component, and a liquid crystal display device including the composition:

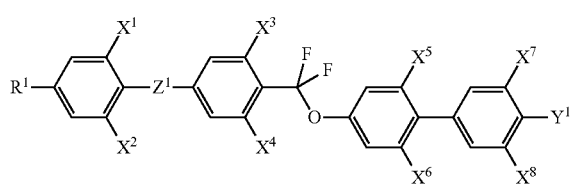

(1)

wherein, $R^1$ is alkyl having 1 to 12 carbons, alkoxy having 1 to 12 carbons or alkenyl having 2 to 12 carbons; $Z^1$ is a single bond, ethylene or carbonyloxy; $X^1$, $X^2$, $X^3$, $X^4$, $X^5$, $X^6$, $X^7$ and $X^8$ are independently hydrogen or fluorine; and $Y^1$ is fluorine, chlorine, alkyl having 1 to 12 carbons in which at least one of hydrogen is replaced by halogen, or alkoxy having 1 to 12 carbons in which at least one of hydrogen is replaced by halogen.

Advantageous Effects of Invention

One of advantages of the invention is to provide a liquid crystal composition satisfying at least one of characteristics such as a high maximum temperature of a nematic phase, a low minimum temperature of the nematic phase, a small viscosity, a suitable optical anisotropy, a large dielectric anisotropy, a large specific resistance, a high stability to ultraviolet light, a high stability to heat and a large elastic constant. Another advantage is to provide a liquid crystal composition having a suitable balance regarding at least two of the characteristics. A further advantage is to provide a liquid crystal display device including such a composition. An additional advantage is to provide an AM device having a short response time, a large voltage holding ratio, a low threshold voltage, a large contrast ratio, a long service life and so forth.

Usage of terms herein is as described below. Terms "liquid crystal composition" and "liquid crystal display device" may be occasionally abbreviated as "composition" and "device," respectively. "Liquid crystal display device" is a generic term for a liquid crystal display panel and a liquid crystal display module. "Liquid crystal compound" is a generic term for a compound having a liquid crystal phase such as a nematic phase or a smectic phase, and a compound having no liquid crystal phase but being mixed to the composition for the purpose of adjusting characteristics such as a temperature range of the nematic phase, viscosity and dielectric anisotropy. The compound has a six-membered ring such as 1,4-cyclohexylene and 1,4-phenylene, and a rod-like molecular structure. "Polymerizable compound" is a compound added for the purpose of forming a polymer in the composition. At least one compound selected from the group of compounds represented by formula (1) may be occasionally abbreviated as "compound (1)." "Compound (1)" means one compound or two or more compounds represented by formula (1). A same rule applies to any other compound represented by any other formula. "At least one" in the context of "replaced" means that not only a position but also the number may be selected without restriction.

The liquid crystal composition is prepared by mixing a plurality of liquid crystal compounds. A ratio (content) of the liquid crystal compound is expressed in terms of weight percent (% by weight) based on the weight of the liquid crystal composition. An additive such as an optically active compound, an antioxidant, an ultraviolet light absorber, a dye, a defoaming agent, a polymerizable compound, a polymerization initiator and a polymerization inhibitor is added to the liquid crystal composition, when necessary. A ratio (amount of addition) of the additive is expressed in term of weight percent (% by weight) based on the weight of the liquid crystal composition in a manner similar to the ratio of the liquid crystal compound. Weight parts per million (ppm) are also used in several cases. A ratio of the polymerization initiator and the polymerization inhibitor is exceptionally expressed based on the weight of the polymerizable compound.

"Maximum temperature of the nematic phase" may be occasionally abbreviated as "maximum temperature." "Minimum temperature of the nematic phase" may be occasionally abbreviated as "minimum temperature." An expression "specific resistance is large" means that the composition has a large specific resistance at room temperature and even at a temperature close to the maximum temperature of the nematic phase in an initial stage, and that the composition has a large specific resistance at room temperature and also at a temperature close to the maximum temperature of the nematic phase even after the device has been used for a long period of time. An expression "voltage holding ratio is large" means that the device has a large voltage holding ratio at room temperature and also at a temperature close to the maximum temperature of the nematic phase in an initial stage, and that the device has a large voltage holding ratio at room temperature and also at a temperature close to the maximum temperature of the nematic phase even after the device has been used for a long period of time.

An expression "at least one of 'A' may be replaced by 'B'" means that the number of 'A' is arbitrary. When the number of 'A' is one, a position of 'A' is arbitrary, and also when the number of 'A' is two or more, positions thereof can be selected without restriction. A same rule also applies to an expression "at least one of 'A' is replaced by 'B'."

A symbol of terminal group R¹ is used for a plurality of compounds in chemical formulas of component compounds. In the compounds, two groups represented by two of arbitrary R¹ may be identical or different. In one case, for example, R¹ of compound (1) is ethyl and R¹ of compound (1-1) is ethyl. In another case, R¹ of compound (1) is ethyl and R¹ of compound (1-1) is propyl. A same rule also applies to a symbol such as R² and X¹. In formula (2), when a is 2, two of ring A exists. In the compound, two rings represented by two of ring A may be identical or different. A same rule also applies to two of arbitrary ring A when a is larger than 2. A same rule also applies to symbol Z², ring C or the like.

Then, 2-fluoro-1,4-phenylene means two divalent groups described below. In the chemical formula, fluorine may be leftward (L) or rightward (R). A same rule also applies to a divalent group of an unsymmetrical ring, such as tetrahydropyran-2,5-diyl.

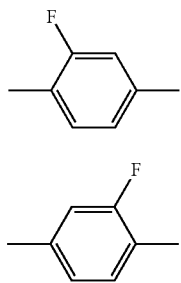

The invention includes the items described below.

Item 1. A liquid crystal composition that has a nematic phase and contains at least one compound selected from the group of compounds represented by formula (1) as a first component:

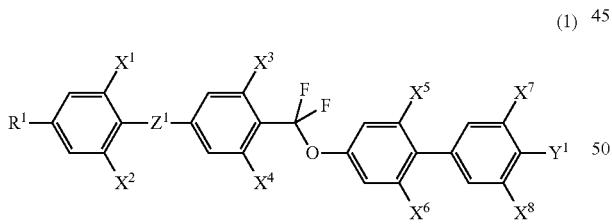

wherein, R¹ is alkyl having 1 to 12 carbons, alkoxy having 1 to 12 carbons or alkenyl having 2 to 12 carbons; Z¹ is a single bond, ethylene or carbonyloxy; $X^1$, $X^2$, $X^3$, $X^4$, $X^5$, $X^6$, $X^7$ and $X^8$ are independently hydrogen or fluorine; and Y¹ is fluorine, chlorine, alkyl having 1 to 12 carbons in which at least one of hydrogen is replaced by halogen or alkoxy having 1 to 12 carbons in which at least one of hydrogen is replaced by halogen.

Item 2. The liquid crystal composition according to item 1, containing at least one compound selected from the group of compounds represented by formula (1-1) to formula (1-10) as the first component:

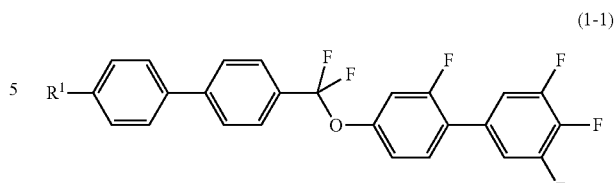
(1-1)

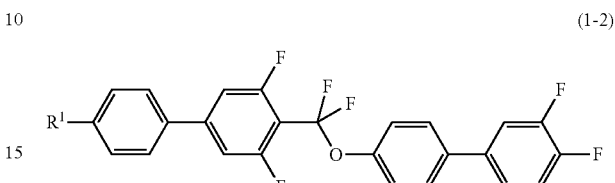
(1-2)

(1-3)

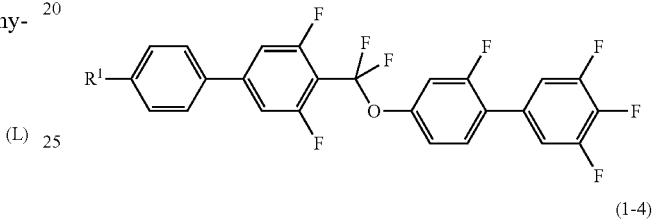
(1-4)

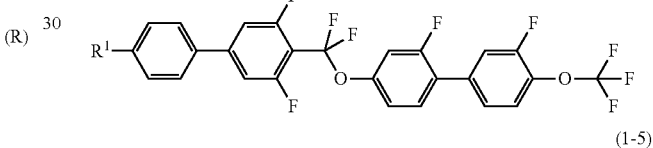
(1-5)

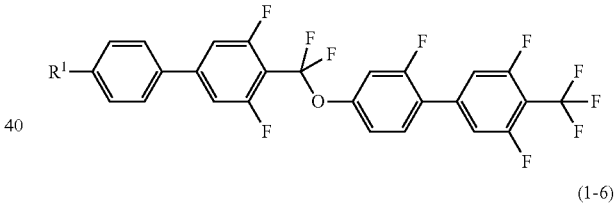
(1-6)

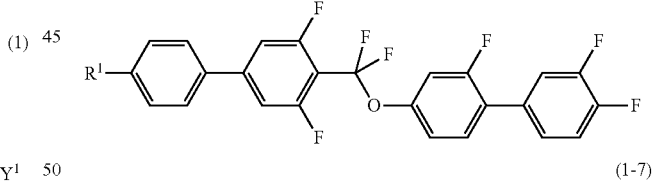
(1-7)

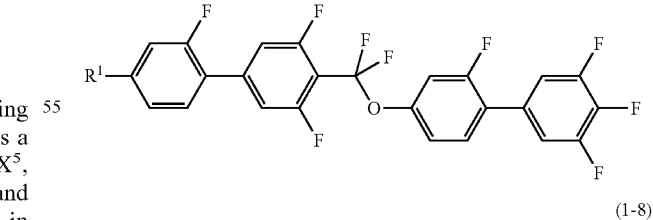
(1-8)

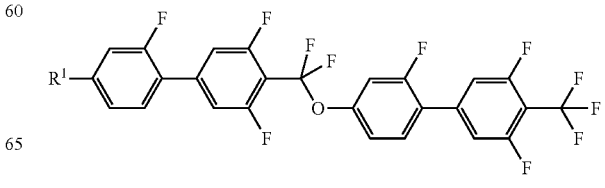

(1-9)

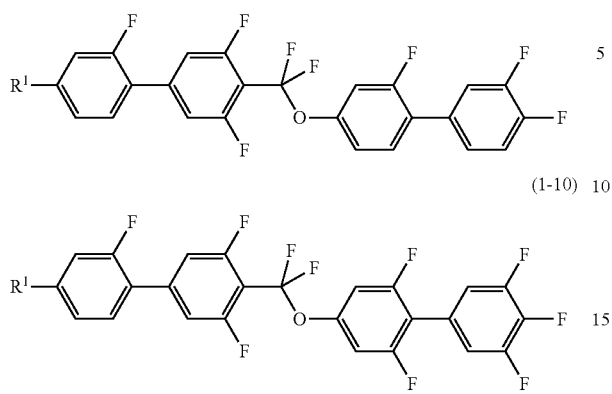

(1-10)

wherein, $R^1$ is alkyl having 1 to 12 carbons, alkoxy having 1 to 12 carbons or alkenyl having 2 to 12 carbons.

Item 3. The liquid crystal composition according to item 1 or 2, wherein a ratio of the first component is in the range of 10% by weight to 40% by weight based on the weight of the liquid crystal composition.

Item 4. The liquid crystal composition according to any one of items 1 to 3, further containing at least one compound selected from the group of compounds represented by formula (2) as a second component:

(2)

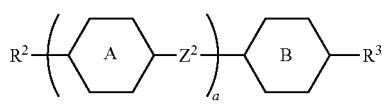

wherein, in formula (2), $R^2$ and $R^3$ are independently alkyl having 1 to 12 carbons, alkoxy having 1 to 12 carbons, alkenyl having 2 to 12 carbons, alkyl having 1 to 12 carbons in which at least one of hydrogen is replaced by fluorine, or alkenyl having 2 to 12 carbons in which at least one of hydrogen is replaced by fluorine; ring A and ring B are independently 1,4-cyclohexylene, 1,4-phenylene, 2-fluoro-1,4-phenylene or 2,5-difluoro-1,4-phenylene; $Z^2$ is a single bond, ethylene or carbonyloxy; and a is 1, 2 or 3.

Item 5. The liquid crystal composition according to any one of items 1 to 4, containing at least one compound selected from the group of compounds represented by formula (2-1) to formula (2-13) as the second component:

(2-1)

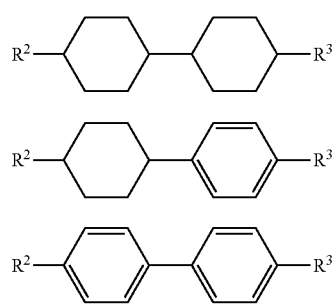

(2-2)

(2-3)

(2-4)

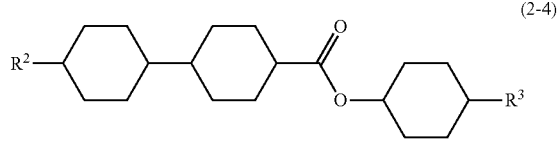

(2-5)

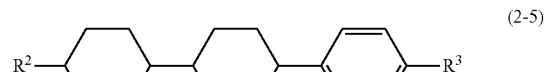

(2-6)

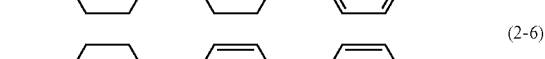

(2-7)

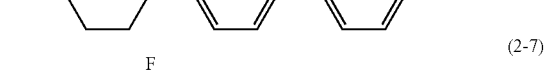

(2-8)

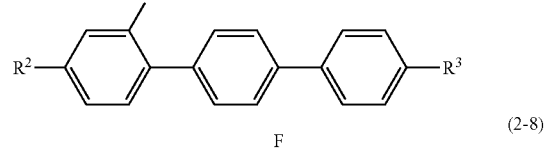

(2-9)

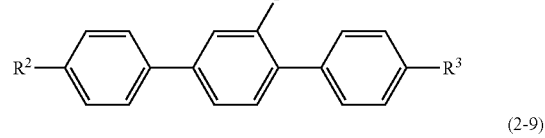

(2-10)

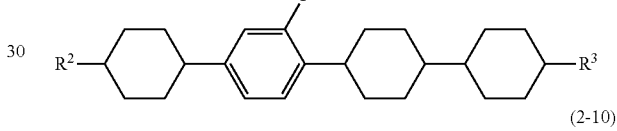

(2-11)

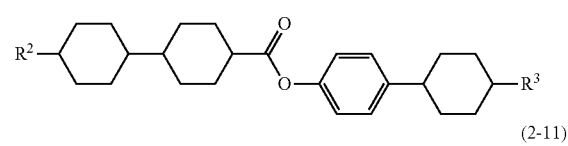

(2-12)

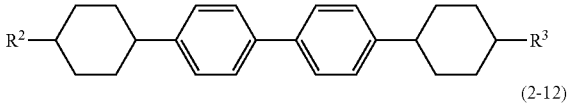

(2-13)

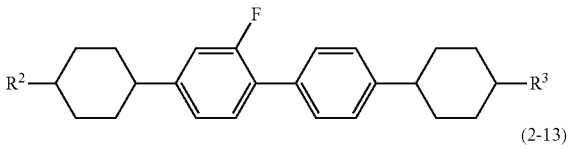

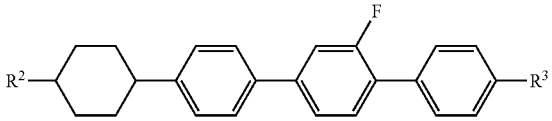

wherein, in formula (2-1) to formula (2-13), $R^2$ and $R^3$ are independently alkyl having 1 to 12 carbons, alkoxy having 1 to 12 carbons, alkenyl having 2 to 12 carbons, alkyl having 1 to 12 carbons in which at least one of hydrogen is replaced by fluorine, or alkenyl having 2 to 12 carbons in which at least one of hydrogen is replaced by fluorine.

Item 6. The liquid crystal composition according to item 4 or 5, wherein a ratio of the second component is in the range of 10% by weight to 90% by weight based on the weight of the liquid crystal composition.

Item 7. The liquid crystal composition according to any one of items 1 to 6, further containing at least one compound selected from the group of compounds represented by formula (3) as a third component:

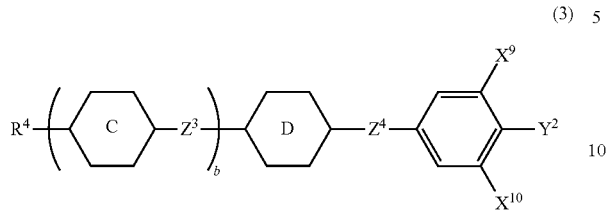
(3)

wherein, in formula (3), $R^4$ is alkyl having 1 to 12 carbons, alkoxy having 1 to 12 carbons or alkenyl having 2 to 12 carbons; ring C and ring D are independently 1,4-cyclohexylene, 1,4-phenylene, 2-fluoro-1,4-phenylene, 2,6-difluoro-1,4-phenylene, pyrimidine-2,5-diyl, 1,3-dioxane-2,5-diyl or tetrahydropyran-2,5-diyl; $Z^3$ and $Z^4$ are independently a single bond, ethylene, carbonyloxy or difluoromethyleneoxy; $X^9$ and $X^{10}$ are independently hydrogen or fluorine; $Y^2$ is fluorine, chlorine, alkyl having 1 to 12 carbons in which at least one of hydrogen is replaced by halogen, or alkoxy having 1 to 12 carbons in which at least one of hydrogen is replaced by halogen; b is 0, 1, 2 or 3; and when b is 2, $Z^3$ is a single bond, ethylene or carbonyloxy.

Item 8. The liquid crystal composition according to any one of items 1 to 7, containing at least one compound selected from the group of compounds represented by formula (3-1) to formula (3-26) as the third component:

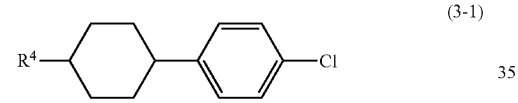
(3-1)

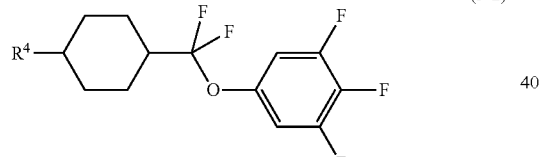
(3-2)

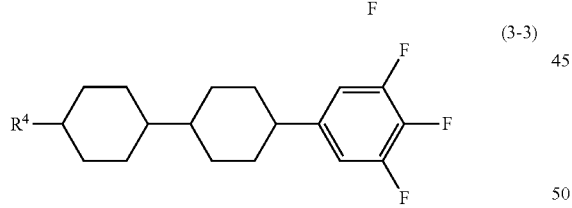
(3-3)

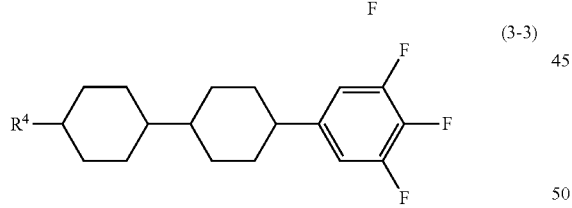
(3-4)

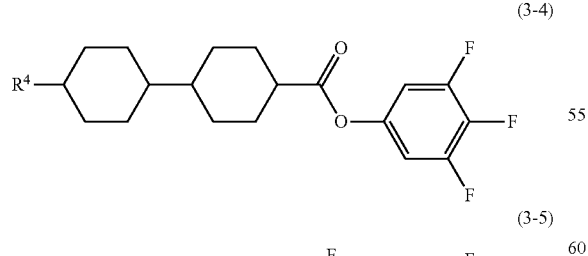
(3-5)

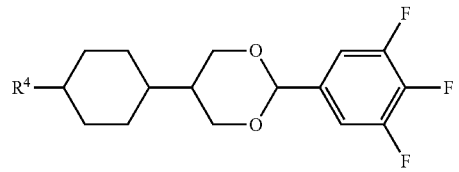
(3-6)

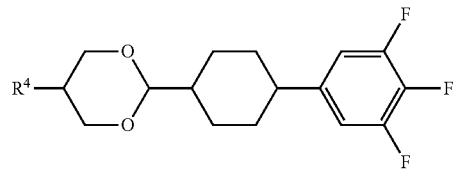
(3-7)

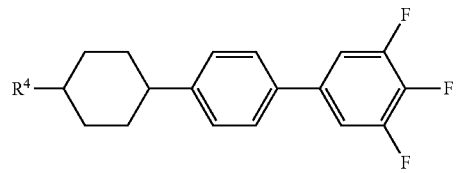
(3-8)

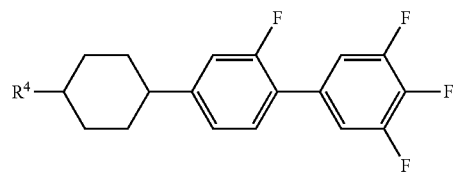
(3-9)

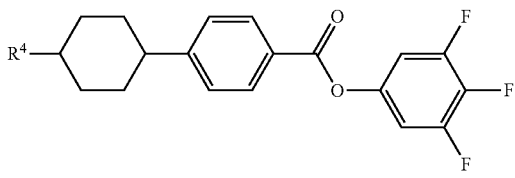
(3-10)

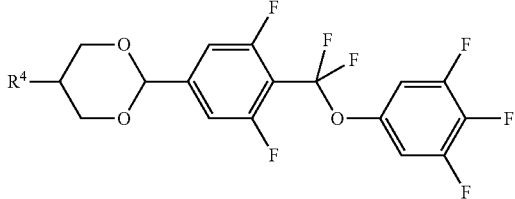
(3-12)

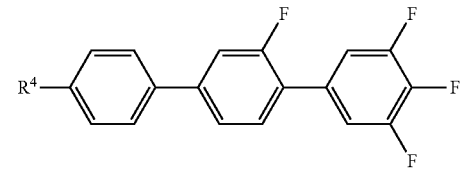
(3-13)

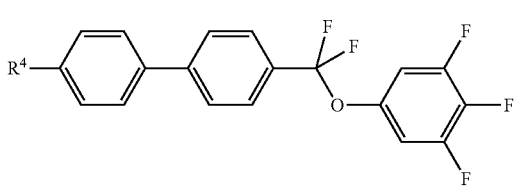
(3-15)

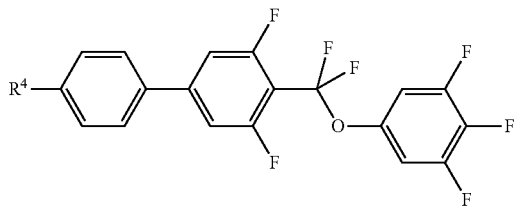
(3-16)

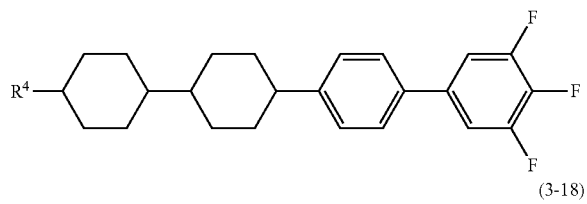
(3-17)

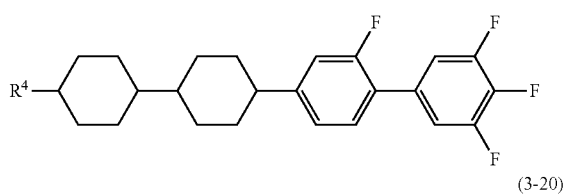
(3-18)

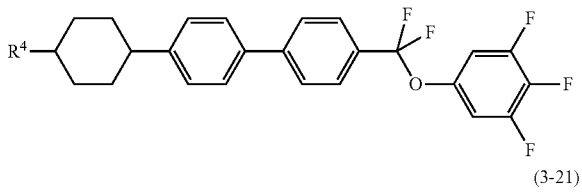
(3-20)

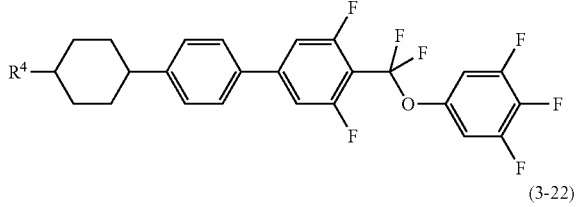
(3-21)

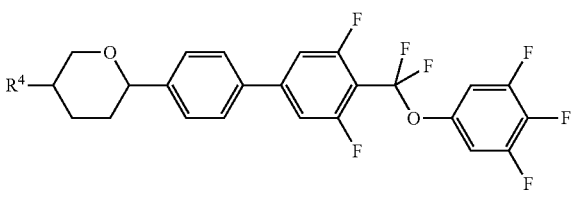
(3-22)

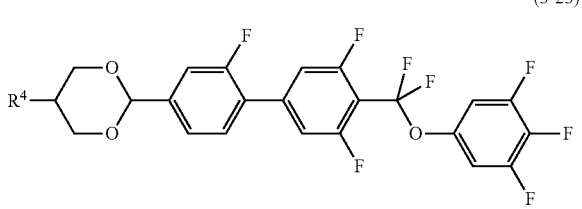
(3-23)

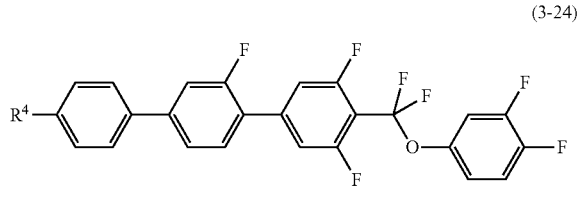
(3-24)

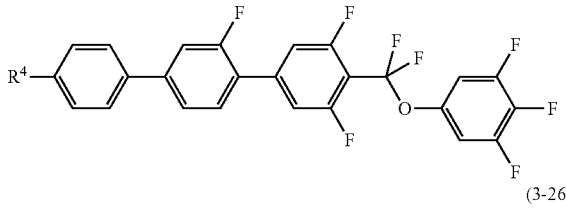
(3-25)

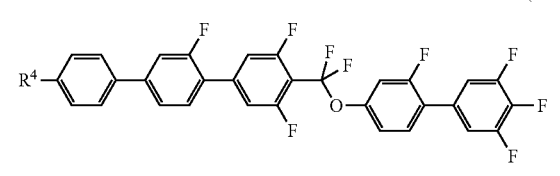
(3-26)

wherein, in formula (3-1) to formula (3-26), $R^4$ is alkyl having 1 to 12 carbons, alkoxy having 1 to 12 carbons or alkenyl having 2 to 12 carbons.

Item 9. The liquid crystal composition according to item 7 or 8, wherein a ratio of the third component is in the range of 10% by weight to 90% by weight based on the weight of the liquid crystal composition.

Item 10. The liquid crystal composition according to any one of items 1 to 9, wherein a maximum temperature of a nematic phase is 70° C. or higher, an optical anisotropy (measured at 25° C.) at a wavelength of 589 nanometers is 0.07 or more, and a dielectric anisotropy (measured at 25° C.) at a frequency of 1 kHz is 2 or more.

Item 11. A liquid crystal display device including the liquid crystal composition according to any one of items 1 to 10.

Item 12. The liquid crystal display device according to item 11, wherein an operating mode in the liquid crystal display device is a TN mode, an ECB mode, an OCB mode, an IPS mode or an FPA mode, and a driving mode in the liquid crystal display device is an active matrix mode.

Item 13. Use of the liquid crystal composition according to any one of items 1 to 10 in a liquid crystal display device.

The invention further includes the following items: (a) the composition further containing at least one of additives, such as an optically active compound, an antioxidant, an ultraviolet light absorber, a dye, a defoaming agent, a polymerizable compound, a polymerization initiator and a polymerization inhibitor; (b) an AM device including the composition; (c) the composition, further containing a polymerizable compound, and a polymer sustained alignment (PSA) mode AM device including the composition; (d) a polymer sustained alignment (PSA) mode AM device, wherein the device includes the composition, and the polymerizable compound in the composition is polymerized; (e) a device including the composition and having a mode of PC, TN, STN, ECB, OCB, IPS, VA, FFS or FPA; (f) a transmissive device including the composition; (g) use of the composition as a composition having a nematic phase; and (h) use of the composition as an optically active composition obtained by adding the optically active compound to the composition.

The composition of the invention will be described in the following order. First, a constitution of the component compounds in the composition will be described. Second, main characteristics of the component compounds and main effects of the compounds on the composition will be described. Third, a combination of components in the composition, a preferred ratio of the components and the basis thereof will be described. Fourth, a preferred embodiment of the component compounds will be described. Fifth, a preferred component compound will be shown. Sixth, an additive that may be added to the composition is described. Seventh, methods for synthesizing the component compounds will be described. Last, an application of the composition will be described.

First, the constitution of the component compounds in the composition will be described. The composition of the invention is classified into composition A and composition B. Composition A may further contain any other liquid crystal compound, the additive or the like in addition to the liquid crystal compound selected from compound (1), compound (2) and compound (3). "Any other liquid crystal compound" means a liquid crystal compound different from compound (1), compound (2) and compound (3). Such a compound is mixed with the composition for the purpose of further adjusting the characteristics. The additive includes the optically active compound, the antioxidant, the ultraviolet light absorber, the dye, the antifoaming agent, the polymerizable compound, the polymerization initiator and the polymerization inhibitor.

Composition B consists essentially of liquid crystal compounds selected from compound (1), compound (2) and compound (3). A term "essentially" means that the composition may also contain the additive, but does not contain any other liquid crystal compound. Composition B has a smaller number of components than composition A has. Composition B is preferred to composition A in view of cost reduction. Composition A is preferred to composition B in view of possibility of further adjusting the characteristics by mixing any other liquid crystal compound.

Second, the main characteristics of the component compounds and the main effects of the compounds on the characteristics of the composition will be described. The main characteristics of the component compounds are summarized in Table 2 on the basis of advantageous effects of the invention. In Table 2, a symbol L stands for "large" or "high," a symbol M stands for "medium," and a symbol S stands for "small" or "low." The symbols L, M and S represent classification based on a qualitative comparison among the component compounds, and 0 (zero) means "value is nearly zero."

TABLE 2

Characteristics of Compounds

| | Compound | | |
|---|---|---|---|
| | (1) | (2) | (3) |
| Maximum temperature | L to M | S to L | S to L |
| Viscosity | M to L | M to L | S to M |
| Optical anisotropy | M to L | M to L | M to L |
| Dielectric anisotropy | L | S to L | 0 |
| Specific resistance | L | L | L |

Upon mixing the component compounds with the composition, the main effects of the component compounds on the characteristics of the composition are as described below. Compound (1) increases the dielectric anisotropy and decreases the minimum temperature. Compound (2) increases the maximum temperature or decreases the viscosity. Compound (3) increases the dielectric anisotropy and decreases the minimum temperature.

Third, the combination of the components in the composition, the preferred ratio of the component compounds and the basis thereof will be described. The combination of the components in the composition includes a combination of the first component and the second component, a combination of the first component and the third component, or a combination of the first component, the second component and the third component. A preferred combination of the components in the composition includes the combination of the first component, the second component and the third component.

A preferred ratio of the first component is about 10% by weight or more for increasing the dielectric anisotropy, and about 40% by weight or less for decreasing the minimum temperature or decreasing the viscosity. A further preferred ratio is in the range of about 10% by weight to about 30% by weight. A particularly preferred ratio is in the range of about 15% by weight to about 25% by weight.

A preferred ratio of the second component is about 10% by weight or more for increasing the maximum temperature or decreasing the viscosity, and about 90% or less for increasing the dielectric anisotropy. A further preferred ratio is in the range of about 20% by weight to about 80% by weight. A particularly preferred ratio is in the range of about 30% by weight to about 70% by weight.

A preferred ratio of the third component is about 10% by weight or more for increasing the dielectric anisotropy, and about 90% by weight or less for decreasing the minimum temperature. A further preferred ratio is in the range of about 20% by weight to about 80% by weight. A particularly preferred ratio is in the range of about 25% by weight to about 70% by weight.

Fourth, the preferred embodiment of the component compounds will be described. $R^1$ and $R^4$ are independently alkyl having 1 to 12 carbons, alkoxy having 1 to 12 carbons or alkenyl having 2 to 12 carbons. Preferred $R^1$ or $R^4$ is alkyl having 1 to 12 carbons for increasing the stability to ultraviolet light or heat. $R^2$ and $R^3$ are independently alkyl having 1 to 12 carbons, alkoxy having 1 to 12 carbons, alkenyl having 2 to 12 carbons, alkyl having 1 to 12 carbons in which at least one of hydrogen is replaced by fluorine, or alkenyl having 2 to 12 carbons in which at least one of hydrogen is replaced by fluorine. Preferred $R^2$ or $R^3$ is alkyl having 1 to 12 carbons for increasing the stability to ultraviolet light or heat, and alkenyl having 2 to 12 carbons for decreasing the minimum temperature or decreasing the viscosity.

Preferred alkyl is methyl, ethyl, propyl, butyl, pentyl, hexyl, heptyl or octyl. Further preferred alkyl is ethyl, propyl, butyl, pentyl or heptyl for decreasing the viscosity.

Preferred alkoxy is methoxy, ethoxy, propoxy, butoxy, pentyloxy, hexyloxy or heptyloxy. Further preferred alkoxy is methoxy or ethoxy for decreasing the viscosity.

Preferred alkenyl is vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl or 5-hexenyl. Further preferred alkenyl is vinyl, 1-propenyl, 3-butenyl or 3-pentenyl for decreasing the viscosity. A preferred configuration of —CH═CH— in the alkenyl depends on a position of a double bond. Trans is preferred in the alkenyl such as 1-propenyl, 1-butenyl, 1-pentenyl, 1-hexenyl, 3-pentenyl and 3-hexenyl for decreasing the viscosity, for instance. Cis is preferred in the alkenyl such as 2-butenyl, 2-pentenyl and 2-hexenyl. In the alkenyl, straight-chain alkenyl is preferred to branched-chain alkenyl.

Preferred examples of alkenyl in which at least one of hydrogen is replaced by fluorine include 2,2-difluorovinyl, 3,3-difluoro-2-propenyl, 4,4-difluoro-3-butenyl, 5,5-difluoro-4-pentenyl or 6,6-difluoro-5-hexenyl. Further preferred examples include 2,2-difluorovinyl or 4,4-difluoro-3-butenyl for decreasing the viscosity.

Ring A and ring B are independently 1,4-cyclohexylene, 1,4-phenylene, 2-fluoro-1,4-phenylene or 2,5-difluoro-1,4-phenylene. Preferred ring A or ring B is 1,4-cyclohexylene for decreasing the viscosity, or 1,4-phenylene for increasing the optical anisotropy. Ring C and ring D are independently 1,4-cyclohexylene, 1,4-phenylene, 2-fluoro-1,4-phenylene, 2,6-difluoro-1,4-phenylene, pyrimidine-2,5-diyl, 1,3-dioxane-2,5-diyl or tetrahydropyran-2,5-diyl. Preferred ring C or ring D is 1,4-phenylene or 2-fluoro-1,4-phenylene for increasing the optical anisotropy. With regard to a configuration of 1,4-cyclohexylene, trans is preferred to cis for increasing the maximum temperature. Tetrahydropyran-2,5-diyl includes:

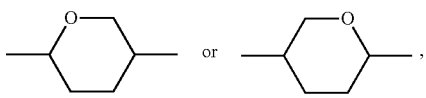

and preferably

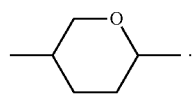

$Z^1$ and $Z^2$ are independently a single bond, ethylene or carbonyloxy. Preferred $Z^1$ or $Z^2$ is a single bond for decreasing the viscosity. $Z^3$ and $Z^4$ are independently a single bond, ethylene, carbonyloxy or difluoromethyleneoxy, and $Z^3$ in case b is 2 is a single bond, ethylene or carbonyloxy. Preferred $Z^3$ or $Z^4$ is a single bond for decreasing the viscosity, and difluoromethyleneoxy for increasing the dielectric anisotropy.

$X^1$, $X^2$, $X^3$, $X^4$, $X^5$, $X^6$, $X^7$, $X^8$, $X^9$ and $X^{10}$ are independently hydrogen or fluorine. Preferred $X^1$, $X^2$, $X^3$, $X^4$, $X^9$, $X^6$, $X^7$, $X^9$, $X^9$ or $X^{10}$ is fluorine for increasing the dielectric anisotropy.

$Y^1$ and $Y^2$ are independently fluorine, chlorine, alkyl having 1 to 12 carbons in which at least one of hydrogen is replaced by halogen, or alkoxy having 1 to 12 carbons in which at least one of hydrogen is replaced by halogen. Preferred $Y^1$ or $Y^2$ is fluorine for decreasing the minimum temperature.

Then, a is 1, 2 or 3. Preferred a is 1 for decreasing the viscosity, and 3 for increasing the maximum temperature. Further, b is 0, 1, 2 or 3. Preferred b is 1 for decreasing the minimum temperature, and 2 for increasing the dielectric anisotropy.

Fifth, the preferred component compounds are shown. Preferred compound (1) includes compound (1-1) to compound (1-10) described in item 2. In the compounds, at least one of the first components is preferably compound (1-2), compound (1-3), compound (1-4), compound (1-6) or compound (1-8). At least two of the first components is preferably a combination of compound (1-1) and compound (1-3), and compound (1-3) and compound (1-8).

Preferred compound (2) includes compound (2-1) to compound (2-13) described in item 5. In the compounds, at least one of the second components is preferably compound (2-1), compound (2-3), compound (2-5), compound (2-6), compound (2-8), compound (2-9) or compound (2-13). At least two of the second components is preferably a combination of compound (2-1) and compound (2-5), compound (2-3) and compound (2-5), compound (2-1) and compound (2-6), compound (2-3) and compound (2-6), compound (2-1) and compound (2-8), or compound (2-3) and compound (2-8).

Preferred compound (3) includes compound (3-1) to compound (3-26) described in item 8. In the compounds, at least one of the third components is compound (3-5), compound (3-11), compound (3-12), compound (3-13), compound (3-15), compound (3-16), compound (3-20), compound (3-23) or compound (3-25). At least two of the third components is preferably a combination of compound (3-12) and compound (3-23), compound (3-13) and compound (3-16), compound (3-15) and compound (3-16), compound (3-16) and compound (3-25), compound (3-20) and compound (3-25), or compound (3-23) and compound (3-25).

Sixth, the additive that may be added to the composition will be described. Such an additive includes the optically active compound, the antioxidant, the ultraviolet light absorber, the dye, the antifoaming agent, the polymerizable compound, the polymerization initiator and the polymerization inhibitor. The optically active compound is added to the composition for the purpose of inducing a helical structure in liquid crystals to give a twist angle. Specific examples of such a compound include compound (4-1) to compound (4-5). A preferred ratio of the optically active compound is about 5% by weight or less. A further preferred ratio is in the range of about 0.01% by weight to about 2% by weight.

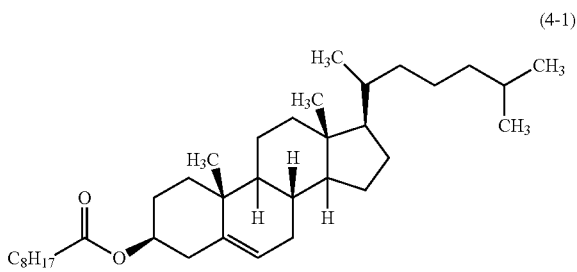

(4-1)

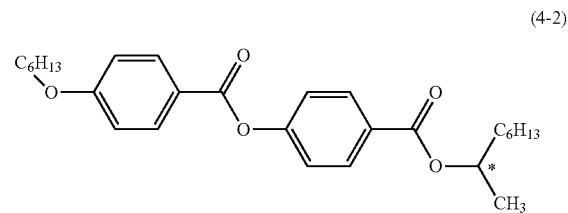

(4-2)

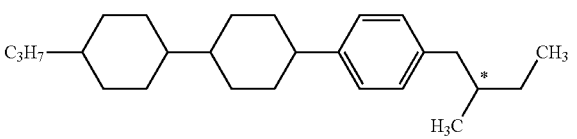

(4-3)

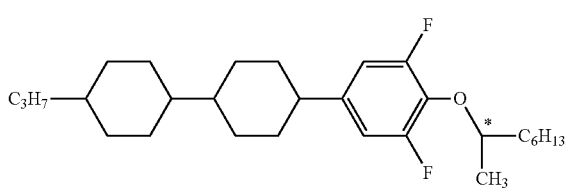

(4-4)

-continued (4-5)

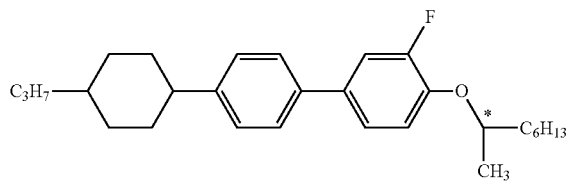

The antioxidant is added to the composition for the purpose of preventing a decrease in specific resistance caused by heating in air, or maintaining a large voltage holding ratio at room temperature and also at a temperature close to the maximum temperature after the device has been used for a long period of time. Preferred examples of the antioxidant include compound (5) where n is an integer from 1 to 9.

(5)

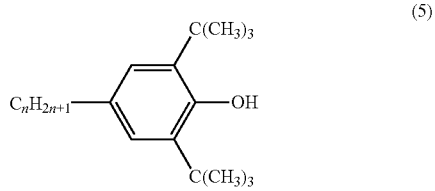

In compound (5), preferred n is 1, 3, 5, 7 or 9. Further preferred n is 7. Compound (5) where n is 7 is effective in maintaining a large voltage holding ratio at room temperature and also at a temperature close to the maximum temperature after the device has been used for a long period of time, because compound (5) has a small volatility. A preferred ratio of the antioxidant is about 50 ppm or more for achieving the effect thereof, and about 600 ppm or less for avoiding a decrease in the maximum temperature or avoiding an increase in the minimum temperature. A further preferred ratio is in the range of about 100 ppm to about 300 ppm.

Specific preferred examples of the ultraviolet light absorber include a benzophenone derivative, a benzoate derivative and a triazole derivative. A light stabilizer such as an amine having steric hindrance is also preferred. A preferred ratio of the ultraviolet light absorber or the stabilizer is about 50 ppm or more for achieving the effect thereof, and about 10,000 ppm or less for avoiding a decrease in the maximum temperature or avoiding an increase in the minimum temperature. A further preferred ratio is in the range of about 100 ppm to about 10,000 ppm.

A dichroic dye such as an azo dye or an anthraquinone dye is added to the composition to be adapted for a device having a guest host (GH) mode. A preferred ratio of the dye is in the range of about 0.01% by weight to about 10% by weight. The antifoaming agent such as dimethyl silicone oil or methyl phenyl silicone oil is added to the composition for preventing foam formation. The preferred ratio of the defoaming agent is about 1 ppm or more for achieving the effect thereof, and about 1,000 ppm or less for avoiding poor display. A further preferred ratio is in the range of about 1 ppm to about 500 ppm.

The polymerizable compound is added to the composition for the purpose of adapting the composition for a device having the polymer sustained alignment (PSA) mode. Specific preferred examples of the polymerizable compound include a compound having a polymerizable group, such as acrylate, methacrylate, a vinyl compound, a vinyloxy compound, propenyl ether, an epoxy compound (oxirane, oxetane) and vinyl ketone. Further preferred examples include an acrylate derivative or a methacrylate derivative. A preferred ratio of the polymerizable compound is about 0.05% by weight or more for achieving the effect thereof, and about 10% by weight or less for avoiding a poor display. A further preferred ratio is in the range of about 0.1% by weight to about 2% by weight. The polymerizable compound is polymerized by irradiation with ultraviolet light or the like. The polymerizable compound may be polymerized in the presence of an initiator such as a photopolymerization initiator. Suitable conditions for polymerization, suitable types of the initiator and suitable amounts thereof are known to those skilled in the art and are described in literature. For example, Irgacure 651 (registered trademark; BASF), Irgacure 184 (registered trademark; BASF) or Darocur 1173 (registered trademark; BASF), each being a photoinitiator, is suitable for radical polymerization. A preferred ratio of the photopolymerization initiator is in the range of about 0.1% by weight to about 5% by weight based on the weight of the polymerizable compound. A further preferred ratio is in the range of about 1% by weight to about 3% by weight.

When the polymerizable compound is stored, the polymerization inhibitor may be added thereto for preventing polymerization. The polymerizable compound is ordinarily added to the composition without removing the polymerization inhibitor. Specific examples of the polymerization inhibitor include hydroquinone, a hydroquinone derivative such as methylhydroquinone, 4-tert-butylcatechol, 4-methoxyphenol and phenothiazine.

Seventh, the methods for synthesizing the component compounds will be described. The compounds can be prepared according to known methods. The examples of synthetic methods will be shown. Compound (1-3) is prepared by the method described in WO 96/11897 A. Compound (2-1) is prepared by the method described in JP S59-176221 A. Compound (2-13) is prepared by the method described in JP H2-237949 A. Compound (3-3) and compound (3-8) are prepared by the method described in JP H2-233626 A. The compound of formula (5) where n is 1 is available from Sigma-Aldrich Corporation. The compound of formula (5) where n is 7 is prepared by the method described in U.S. Pat. No. 3,660,505 B.

Any compounds whose synthetic methods are not described above can be prepared according to the methods described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza in Japanese) (Maruzen Co., Ltd.). The composition is prepared according to publicly known methods using the thus obtained compounds. For example, the component compounds are mixed and dissolved in each other by heating.

Last, the application of the composition will be described. The composition of the invention mainly has a minimum temperature of about −10° C. or lower, a maximum temperature of about 70° C. or higher, and an optical anisotropy in the range of about 0.07 to about 0.20. The device including the composition has a large voltage holding ratio. The composition is suitable for use in the AM device. The composition is particularly suitable for use in a transmissive AM device. A composition having an optical anisotropy in the range of about 0.08 to about 0.25, and also a composition having an optical anisotropy in the range of about 0.10 to about 0.30 may be prepared by controlling the ratio of the component compounds or by mixing with any other liquid crystal compound. The composition can be used as a composition having the nematic phase, and can be used as an optically active composition by adding the optically active compound.

The composition can be used for the AM device. The composition can also be used for a PM device. The composition can also be used for an AM device and a PM device having a mode such as PC, TN, STN, ECB, OCB, IPS, FFS, VA or FPA. Use for the AM device having the TN, OCB, IPS or FFS mode is particularly preferred. When no voltage is applied in the AM device having the IPS mode or FFS mode, the alignment of liquid crystal molecules may be parallel to a glass substrate, or may be vertical. The device may be of a reflective type, a transmissive type or a transflective type. Use for the transmissive device is preferred. The composition can also be used for an amorphous silicon-TFT device or a polycrystal silicon-TFT device. The composition can also be used for a nematic curvilinear aligned phase (NCAP) device prepared by microencapsulating the composition, and for a polymer dispersed (PD) device in which a three-dimensional network polymer is formed in the composition.

EXAMPLES

The invention will be described in more detail by way of Examples. The invention is not limited by the Examples. The invention contains a mixture of the composition in Example 1 and the composition in Example 2. The invention also contains a mixture of at least two compositions in Examples. Prepared compounds were identified by a method such as an NMR analysis. Characteristics of the compounds and compositions were measured by the methods described below.

NMR analysis: For measurement, DRX-500 made by Bruker BioSpin Corporation was used. In $^1$H-NMR measurement, samples were dissolved in a deuterated solvent such as $CDCl_3$, and measurement was carried out under conditions of room temperature, 500 MHz and 16 times of accumulation. In $^{19}$F-NMR measurement, $CFCL_3$ was used as an internal standard under accumulation of 24 times. In explaining nuclear magnetic resonance spectra, s, d, t, q, quin, sex, m and br stand for a singlet, a doublet, a triplet, a quartet, a quintet, a sextet, a multiplet and broad, respectively.

Gas chromatographic analysis: GC-14B Gas Chromatograph made by Shimadzu Corporation was used for measurement. A carrier gas was helium (2 mL per minute). A sample injector and a detector (FID) were set to 280° C. and 300° C., respectively. A capillary column DB-1 (length 30 m, bore 0.32 mm, film thickness 0.25 μm; dimethylpolysiloxane as a stationary phase, non-polar) made by Agilent Technologies, Inc. was used for separation of component compounds. After the column was kept at 200° C. for 2 minutes, the column was heated to 280° C. at a rate of 5° C. per minute. A sample was prepared in an acetone solution (0.1% by weight), and then 1 microliter of the solution was injected into the sample injector. A recorder was C-R5A Chromatopac made by Shimadzu Corporation or the equivalent thereof. The resulting gas chromatogram showed a retention time of a peak and a peak area corresponding to each of the component compounds.

As a solvent for diluting a sample, chloroform, hexane and so forth may also be used. The following capillary columns may also be used for separating component compounds: HP-1 (length 30 m, bore 0.32 mm, film thickness 0.25 μm) made by Agilent Technologies, Inc., Rtx-1 (length 30 m, bore 0.32 mm, film thickness 0.25 μm) made by Restek Corporation and BP-1 (length 30 m, bore 0.32 mm, film thickness 0.25 μm) made by SGE International Pty. Ltd. A capillary column CBP1-M50-025 (length 50 m, bore 0.25 mm, film thickness 0.25 μm) made by Shimadzu Corporation may also be used for the purpose of avoiding an overlap of peaks of the compounds.

A ratio of liquid crystal compounds contained in a composition may be calculated by the method as described below. A mixture of liquid crystal compounds is detected using a gas chromatograph (FID). A ratio of peak areas in a gas chromatogram corresponds to a ratio of the liquid crystal compounds (weight ratio). When the capillary columns described above were used, a correction coefficient of each of the liquid crystal compounds may be regarded as 1 (one). Accordingly, a ratio (% by weight) of the liquid crystal compounds can be calculated from the ratio of the peak areas.

Sample for measurement: When characteristics of a composition were measured, the composition was measured as was. When characteristics of a compound were measured, a sample for measurement was prepared by mixing the compound (15% by weight) into a base liquid crystal (85% by weight). Values of characteristics of the compound were calculated according to an extrapolation method using values obtained by measurement: (Extrapolated value)={(measured value of a sample)–0.85×(measured value of base liquid crystal)}/0.15. When a smectic phase (or crystals) precipitated at the ratio thereof at 25° C., a ratio of the compound to the base liquid crystal was changed step by step in the order of (10% by weight:90% by weight), (5% by weight:95% by weight) and (1% by weight:99% by weight). Values of maximum temperature, optical anisotropy, viscosity and dielectric anisotropy with regard to the compound were determined according to the extrapolation method.

The base liquid crystal described below was used. A ratio of the component compounds is shown in terms of weight percent.

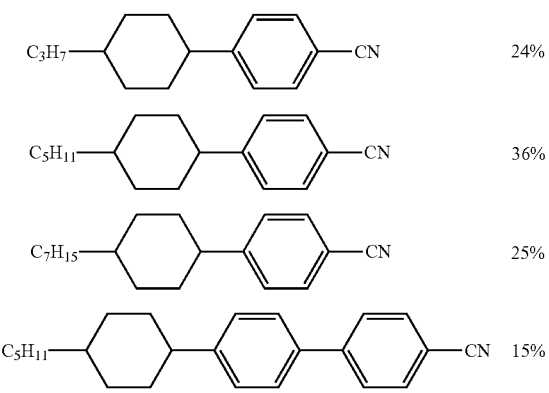

Measuring method: Characteristics were measured according to the methods described below. Most of the methods are applied as described in the JEITA Standard (JEITA ED-2521B) discussed and established by the Japan Electronics and Information Technology Industries Association (hereafter referred to as JEITA), or as modified thereon. No TFT was attached to a TN device used for measurement.

(1) Maximum temperature of nematic phase (NI; ° C.): A sample was placed on a hot plate in a melting point apparatus equipped with a polarizing microscope and was heated at a rate of 1° C. per minute. Temperature when part of the sample began to change from a nematic phase to an isotropic liquid was measured.

(2) Minimum temperature of nematic phase ($T_c$; ° C.): A sample having a nematic phase was put in glass vials and kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., $T_c$ was expressed as $T_c$<−20° C.

(3) Viscosity (bulk viscosity; η; measured at 20° C.; mPa·s): A cone-plate (E type) rotational viscometer made by Tokyo Keiki Inc. was used for measurement.

(4) Viscosity (rotational viscosity; γ1; measured at 25° C.; mPa·s): Measurement was carried out according to the method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. A voltage was stepwise applied to the device in the range of 16 V to 19.5 V at an increment of 0.5 V. After a period of 0.2 second with no voltage application, application was repeated under the conditions of only one rectangular wave (rectangular pulse; 0.2 second) and no application (2 seconds). A peak current and a peak time of a transient current generated by the application were measured. A value of the rotational viscosity was obtained from the measured values and a calculation equation (8) on page 40 of the paper presented by M. Imai et al. A value of dielectric anisotropy necessary for the calculation was determined according to a method as described below by using the device used for measuring the rotational viscosity.

(5) Optical anisotropy (refractive index anisotropy; Δn; measured at 25° C.): Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy was calculated from an equation: Δn=n∥−n⊥.

(6) Dielectric anisotropy (Δε; measured at 25° C.): A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant (E∥) in the major axis direction of liquid crystal molecules was measured. Sine waves (0.5 V, 1 kHz) were applied to the device, and after 2 seconds, a dielectric constant (ε⊥) in the minor axis direction of the liquid crystal molecules was measured. A value of dielectric anisotropy was calculated from an equation: Δε=ε∥−ε⊥.

(7) Threshold voltage (Vth; measured at 25° C.; V): An LCD-5100 luminance meter made by Otsuka Electronics Co., Ltd. was used for measurement. A light source was a halogen lamp. A sample was put in a TN device having a normally white mode, in which a distance (cell gap) between two glass substrates was 0.45/Δn micrometers and a twist angle was 80 degrees. Voltage (32 Hz, rectangular waves) to be applied to the device was stepwise increased from 0 V to 10 V at an increment of 0.02 V. On the occasion, the device was irradiated with light from a direction perpendicular to the device, and the amount of light passing through the device was measured. A voltage-transmittance curve was prepared, in which the maximum amount of light corresponds to 100% transmittance and the minimum amount of light corresponds to 0% transmittance. A threshold voltage was expressed as voltage at 90% transmittance.

(8) Voltage holding ratio (VHR-1; measured at 25° C.; %): A TN device used for measurement had a polyimide alignment film, and a distance (cell gap) between two glass substrates was 5 micrometers. A sample was put in the device, and then the device was sealed with an ultraviolet-curable adhesive. A pulse voltage (60 microseconds at 5 V) was applied to the TN device and the device was charged. A decaying voltage was measured for 16.7 milliseconds with a high-speed voltmeter, and area A between a voltage curve and a horizontal axis in a unit cycle was obtained. Area B was an area without decay. A voltage holding ratio was expressed as a percentage of area A to area B.

(9) Voltage holding ratio (VHR-2; measured at 80° C.; %): A voltage holding ratio was measured in the same procedure as the above except that the measurement was made at 80° C. in place of 25° C. The obtained value was expressed as VHR-2.

(10) Voltage holding ratio (VHR-3; measured at 25° C.; %): Stability to ultraviolet light was evaluated by measuring a voltage holding ratio after ultraviolet light irradiation. A TN device used for measurement had a polyimide alignment film and a cell gap was 5 micrometers. A sample was injected into the device, and then the device was irradiated with light for 20 minutes. A light source was an ultra high-pressure mercury lamp USH-500D (made by Ushio, Inc.), and a distance between the device and the light source was 20 centimeters. In measuring VHR-3, a decaying voltage was measured for 16.7 milliseconds. A composition having a large VHR-3 has a large stability to ultraviolet light. A value of VHR-3 is preferably 90% or more, and further preferably 95% or more.

(11) Voltage holding ratio (VHR-4; measured at 25° C.; %): A TN device into which a sample was injected was heated in a constant-temperature bath at 80° C. for 500 hours, and then stability to heat was evaluated by measuring a voltage holding ratio. In measuring VHR-4, a decaying voltage was measured for 16.7 milliseconds. A composition having a large VHR-4 has a large stability to heat.

(12) Response time (τ; measured at 25° C.; ms): An LCD-5100 luminance meter made by Otsuka Electronics Co., Ltd. was used for measurement. A light source was a halogen lamp. A low-pass filter was set at 5 kHz. A sample was put in a TN device having a normally white mode in which a distance (cell gap) between two glass substrates was 5.0 micrometers and a twist angle was 80 degrees. Rectangular waves (60 Hz, 5 V, 0.5 second) were applied to the device. On the occasion, the device was irradiated with light from a direction perpendicular to the device, and the amount of light passing through the device was measured. The maximum amount of light was regarded as 100% transmittance, and the minimum amount of light as 0% transmittance. Rise time (τr; ms) is the time taken for transmittance to change from 90% to 10%. Fall time (τf; ms) is the time taken for transmittance to change from 10% to 90%. Response time was expressed as a sum of the rise time and fall time thus obtained.

(13) Elastic constant (K; measured at 25° C.; pN): HP4284A LCR Meter made by Yokogawa and Hewlett Packard Co. was used for measurement. A sample was put in a homogeneously aligned device in which a distance (cell gap) between two glass substrates was 20 micrometers. A charge of 0 volts to 20 volts was applied to the device, and electrostatic capacity and applied voltage were measured. Measured values of electrostatic capacity (C) and applied voltage (V) were fitted to equation (2.98) and equation (2.101) on page 75 of the "Liquid Crystal Device Handbook (Ekisho Debaisu Handobukku, in Japanese)" (The Nikkan Kogyo Shimbun, Ltd.), and a value of K11 and K33 were obtained from equation (2.99). Next, K22 was calculated using the values of K11 and K33 thus obtained in formula (3.18) on page 171. The elastic constant was expressed in terms of the mean value of K11, K22 and K33 thus obtained.

(14) Specific resistance (p; measured at 25° C.; Ωcm): Into a vessel equipped with electrodes, 1.0 milliliter of sample was injected. A DC voltage (10 V) was applied to the vessel, and a DC current after 10 seconds was measured. A specific resistance was calculated from the following equation: (Specific resistance)={(voltage)×(electric capacity of a vessel)}/{(direct current)×(dielectric constant of vacuum)}.

(15) Helical pitch (P; measured at room temperature; μm): A helical pitch was measured according to a wedge method. Refer to page 196 in "Handbook of Liquid Crystals (Ekisho Binran in Japanese)" (issued in 2000, Maruzen Co., Ltd.). A sample was injected into a wedge cell and left to stand at room temperature for 2 hours, and then a gap (d2−d1) between disclination lines was observed by a polarizing microscope (trade name: MM40/60 Series, Nikon Corporation). A helical pitch (P) was calculated according to the following equation in which an angle of the wedge cell was expressed as θ: P=2×(d2−d1)×tan θ.

(16) Dielectric anisotropy in minor axis direction (ε⊥; measured at 25° C.): A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (ε⊥) in the minor axis direction of the liquid crystal molecules was measured.

The compounds described in Examples were expressed using symbols according to definitions in Table 3 below. In Table 3, a configuration of 1,4-cyclohexylene is trans. A parenthesized number next to a symbolized compound corresponds to the number of the compound. A symbol (-) means any other liquid crystal compound. The ratio (percent) of the liquid crystal compound means "weight percent (% by weight)" based on the weight of the liquid crystal composition. Last, values of characteristics of the composition were summarized.

TABLE 3

| Method for Description of Compounds using Symbols R—(A$_1$)—Z$_1$— . . . —Z$_n$—(A$_n$)—R' | |
|---|---|
| 1) Left-terminal Group R— | Symbol |
| $C_nH_{2n+1}$— | n- |
| $C_nH_{2n+1}O$— | nO— |
| $C_mH_{2m+1}OC_nH_{2n}$— | mOn— |
| $CH_2$=CH— | V— |
| $C_nH_{2n+1}$—CH=CH— | nV— |
| $CH_2$=CH—$C_nH_{2n}$— | Vn— |
| $C_mH_{2m+1}$—CH=CH—$C_nH_{2n}$— | mVn— |
| $CF_2$=CH— | VFF— |
| $CF_2$=CH—$C_nH_{2n}$— | VFFn— |
| 2) Right-terminal Group —R' | Symbol |
| —$C_nH_{2n+1}$ | -n |
| —$OC_nH_{2n+1}$ | —On |
| —CH=$CH_2$ | —V |
| —CH=CH—$C_nH_{2n+1}$ | —Vn |
| —$C_nH_{2n}$—CH=$CH_2$ | —nV |

TABLE 3-continued

| Method for Description of Compounds using Symbols R—(A$_1$)—Z$_1$— . . . —Z$_n$—(A$_n$)—R' | |
|---|---|
| —$C_nH_{2n}$—CH=CH—$C_mH_{2m+1}$ | —nVm |
| —CH=$CF_2$ | —VFF |
| —COOCH$_3$ | —EMe |
| —F | —F |
| —Cl | —CL |
| —OCF$_3$ | —OCF3 |
| —CF$_3$ | —CF3 |
| —CN | —C |
| —OCH=CH—$CF_2$H | —OVCF2H |
| —OCH=CH—CF$_3$ | —OVCF3 |
| 3) Bonding Group —Z$_n$— | Symbol |
| —$C_2H_4$— | 2 |
| —COO— | E |
| —CH=CH— | V |
| —C≡C— | T |
| —$CF_2$O— | X |
| —$CH_2$O— | 1O |
| 4) Ring Structure —A$_n$— | Symbol |
| cyclohexylene | H |
| tetrahydropyran (O top) | Dh |
| tetrahydropyran (O bottom) | dh |
| phenylene | B |
| fluorophenylene | B(F) |
| 2-fluorophenylene | B(2F) |
| difluorophenylene | B(F,F) |
| 2,5-difluorophenylene | B(2F,5F) |

TABLE 3-continued

Method for Description of Compounds using Symbols
R—(A$_1$)—Z$_1$— ... —Z$_n$—(A$_n$)—R'

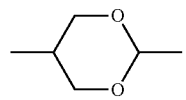 G

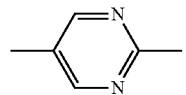 Py

5) Examples of Description

Example 1  3-HH-V1

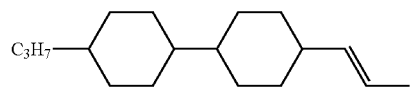

Example 2  3-BB(F)B(F,F)-F

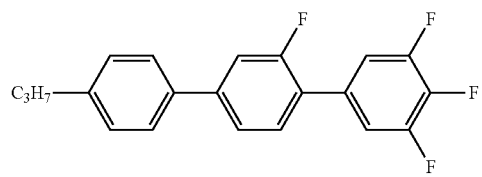

Example 3  4-BB(F)B(F,F)XB(F,F)-F

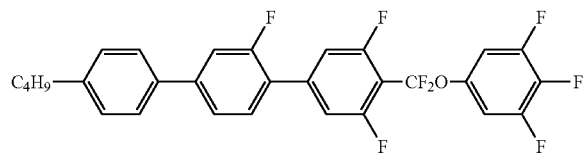

Example 4  3-BB(F,F)XB(F)B(F,F)-F

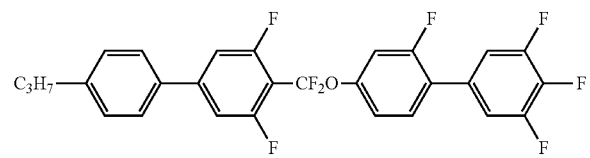

Comparative Example 1

Example 1 was selected from the compositions disclosed in WO 2011-062049. The reason is that the composition contains compound (2) and compound (3), and has the largest dielectric anisotropy. Components and characteristics of the composition are as described below.

| | | |
|---|---|---|
| 3-HH-V | (2-1) | 38% |
| 3-HH-V1 | (2-1) | 10% |
| 1V2-HHB-1 | (2-5) | 10% |
| 3-HHEBH-3 | (2-10) | 4% |
| 3-HHB(F,F)-F | (3-3) | 4% |
| 3-HGB(F,F)-F | (3-6) | 7% |
| 3-BB(F,F)XB(F,F)-F | (3-16) | 9% |
| 2-HBB(F,F)-F | (3-17) | 4% |
| 3-HHBB(F,F)-F | (3-17) | 3% |
| 4-BB(F)B(F,F)XB(F,F)-F | (3-25) | 7% |
| 3-HHB-F | (3) | 4% |

NI=93.1° C.; Tc≤−20° C.; Δn=0.089; Δε=4.3; γ1=62.4 mPa·s; K11=11.8 pN; K22=8.5 pN; K33=20.0 pN; K=13.4 pN; VHR-1=99.6%; VHR-2=99.0%; VHR-3=98.9%.

Example 1

| | | |
|---|---|---|
| 3-BB(F,F)XB(F)B(F,F)-CF3 | (1-5) | 3% |
| 3-BB(F,F)XB(F)B(F)-F | (1-6) | 3% |
| 5-B(F)B(F,F)XB(F)B(F)-F | (1-9) | 5% |
| 3-HH-O1 | (2-1) | 3% |
| 3-HH-V | (2-1) | 33% |
| 1V2-HH-3 | (2-1) | 5% |
| V2-HHB-1 | (2-5) | 3% |
| 3-BB(F)B-2V | (2-8) | 5% |
| 5-HB(F)BH-3 | (2-12) | 7% |
| 5-HGB(F,F)-F | (3-6) | 3% |
| 3-GHB(F,F)-F | (3-7) | 7% |
| 3-HBEB(F,F)-F | (3-10) | 3% |
| 3-BB(F,F)XB(F,F)-F | (3-16) | 8% |
| 3-HBBXB(F,F)-F | (3-20) | 5% |
| 4-GB(F)B(F,F)XB(F,F)-F | (3-23) | 4% |
| 5-GB(F)B(F,F)XB(F,F)-F | (3-23) | 3% |

NI=79.9° C.; Tc<−30° C.; Δn=0.106; Δε=10.4; Vth=1.41 V; η=12.4 mPa·s.

Example 2

| | | |
|---|---|---|
| 3-BB(F,F)XB(F)B(F,F)-F | (1-3) | 15% |
| 3-HH-V | (2-1) | 27% |
| 3-HH-V1 | (2-1) | 9% |
| 1V2-HH-1 | (2-1) | 7% |
| 1V-HBB-2 | (2-6) | 6% |
| 3-GB(F,F)XB(F,F)-F | (3-12) | 5% |
| 3-BB(F)B(F,F)-CF3 | (3-14) | 3% |
| 3-HBBXB(F,F)-F | (3-20) | 7% |
| 5-HBB(F,F)XB(F,F)-F | (3-21) | 3% |
| 4-GB(F)B(F,F)XB(F,F)-F | (3-23) | 6% |
| 3-BB(F)B(F,F)XB(F)-F | (3-24) | 3% |
| 3-BB(F)B(F,F)XB(F,F)-F | (3-25) | 3% |
| 4-BB(F)B(F,F)XB(F,F)-F | (3-25) | 6% |

NI=78.2° C.; Tc<−30° C.; Δn=0.118; Δε=13.9; Vth=1.26 V; η=14.6 mPa·s.

Example 3

| | | |
|---|---|---|
| 3-BB(F,F)XB(F)B(F,F)-F | (1-3) | 10% |
| 3-BB(F,F)XB(F)B(F)-OCF3 | (1-4) | 6% |
| 3-HH-V | (2-1) | 37% |
| 2-BB(F)B-3 | (2-8) | 5% |
| 2-BB(F)B-2V | (2-8) | 5% |
| 3-HB-CL | (3-1) | 4% |
| 3-HHXB(F,F)-F | (3-5) | 4% |
| 3-BB(F)XB(F,F)-F | (3-16) | 6% |
| 4-GBB(F)B(F,F)-F | (3-19) | 3% |
| 3-HBBXB(F,F)-F | (3-20) | 4% |
| 5-HBBXB(F,F)-F | (3-20) | 5% |
| 3-BB(F)B(F,F)XB(F)-F | (3-24) | 5% |
| 4-BB(F)B(F,F)XB(F)-F | (3-24) | 3% |
| 5-BB(F)B(F,F)XB(F)B(F,F)-F | (3-26) | 3% |

NI=79.5° C.; Tc<−30° C.; Δn=0.130; Δε=11.5; Vth=1.39 V; η=13.3 mPa·s.

Example 4

| | | |
|---|---|---|
| 3-BB(F,F)XB(F)B(F)-OCF3 | (1-4) | 5% |
| 5-B(F)B(F,F)XB(F)B(F,F)-F | (1-7) | 5% |
| 3-HH-V | (2-1) | 35% |
| 3-HH-V1 | (2-1) | 3% |
| 3-HH-VFF | (2-1) | 4% |
| 1-BB-3 | (2-3) | 3% |
| V-HHB-1 | (2-5) | 3% |
| 1V-HBB-2 | (2-6) | 4% |
| 5-B(F)BB-2 | (2-7) | 3% |
| 5-HBB(F)B-3 | (2-13) | 3% |
| 5-HXB(F,F)-F | (3-2) | 3% |
| 5-HHBB(F,F)-F | (3-17) | 5% |
| 3-HBB(F,F)XB(F,F)-F | (3-21) | 5% |
| 4-GB(F)B(F,F)XB(F,F)-F | (3-23) | 4% |
| 5-GB(F)B(F,F)XB(F,F)-F | (3-23) | 3% |
| 4-BB(F)B(F,F)XB(F,F)-F | (3-25) | 8% |
| 5-BB(F)B(F,F)XB(F,F)-F | (3-25) | 4% |

NI=83.6° C.; Tc<−30° C.; Δn=0.118; Δε=10.3; Vth=1.43 V; η=11.8 mPa·s.

Example 5

| | | |
|---|---|---|
| 3-BBXB(F)B(F,F)-F | (1-1) | 7% |
| 4-BB(F,F)XB(F)B(F,F)-F | (1-3) | 3% |
| 5-BB(F,F)XB(F)B(F,F)-F | (1-3) | 3% |
| 3-B(F)B(F,F)XB(F)B(F,F)-CF3 | (1-8) | 3% |
| 2-HH-3 | (2-1) | 5% |
| 3-HH-V | (2-1) | 33% |
| 7-HB-1 | (2-2) | 3% |
| V2-HHB-1 | (2-5) | 7% |
| 5-HBB(F)B-2 | (2-13) | 4% |
| 3-HHB(F,F)-F | (3-3) | 5% |
| 3-BBXB(F,F)-F | (3-15) | 5% |
| 3-HBB(F,F)XB(F,F)-F | (3-21) | 5% |
| 5-HBB(F,F)XB(F,F)-F | (3-21) | 7% |
| 3-BB(F)B(F,F)XB(F,F)-F | (3-25) | 3% |
| 4-BB(F)B(F,F)XB(F,F)-F | (3-25) | 7% |

NI=82.9° C.; Tc<−30° C.; Δn=0.116; Δε=11.7; Vth=1.39 V; η=10.5 mPa·s.

Example 6

| | | |
|---|---|---|
| 3-BBXB(F)B(F,F)-F | (1-1) | 6% |
| 2-B(F)B(F,F)XB(F)B(F,F)-F | (1-7) | 3% |
| 4-B(F)B(F,F)XB(F)B(F,F)-CF3 | (1-8) | 4% |
| 5-HH-V | (2-1) | 18% |
| 3-HH-V1 | (2-1) | 10% |
| 1V2-HH-3 | (2-1) | 5% |
| 3-HB-O2 | (2-2) | 10% |
| 2-BB(F)B-3 | (2-8) | 4% |
| 3-HHXB(F,F)-F | (3-5) | 7% |
| 3-BB(F)B(F,F)-F | (3-13) | 4% |
| 4-HHB(F)B(F,F)-F | (3-18) | 3% |
| 3-HBBXB(F,F)-F | (3-20) | 8% |
| 5-HBBXB(F,F)-F | (3-20) | 5% |
| 3-BB(F)B(F,F)XB(F,F)-F | (3-25) | 3% |
| 4-BB(F)B(F,F)XB(F,F)-F | (3-25) | 7% |
| 5-BB(F)B(F,F)XB(F,F)-F | (3-25) | 3% |

NI=88.9° C.; Tc<−30° C.; Δn=0.127; Δε=12.6; Vth=1.42 V; η=16.1 mPa·s.

Example 7

| | | |
|---|---|---|
| 3-BB(F,F)XBB(F,F)-F | (1-2) | 7% |
| 2-B(F)B(F,F)XB(F)B(F,F)-F | (1-7) | 3% |
| 3-B(F)B(F,F)XB(F)B(F,F)-F | (1-7) | 3% |
| 3-HH-V | (2-1) | 41% |
| 4-HHEH-3 | (2-4) | 3% |
| VFF-HHB-1 | (2-5) | 3% |
| 3-HB(F)HH-2 | (2-9) | 5% |
| 3-HHEB(F,F)-F | (3-4) | 5% |
| 3-BB(F)B(F,F)-CF3 | (3-14) | 4% |
| 3-BB(F,F)XB(F,F)-F | (3-16) | 5% |
| 3-HHBB(F,F)-F | (3-17) | 3% |
| 5-GBB(F)B(F,F)-F | (3-19) | 3% |
| 3-HBBXB(F,F)-F | (3-20) | 5% |
| 4-GB(F)B(F,F)XB(F,F)-F | (3-23) | 6% |
| 5-GB(F)B(F,F)XB(F,F)-F | (3-23) | 4% |

NI=84.9° C.; Tc<−30° C.; Δn=0.104; Δε=12.0; Vth=1.33 V; η=17.4 mPa·s.

Example 8

| | | |
|---|---|---|
| 5-BB(F,F)XB(F)B(F,F)-F | (1-3) | 3% |
| 3-BB(F,F)XB(F)B(F)-F | (1-6) | 5% |
| 5-B(F)B(F,F)XB(F)B(F,F)-F | (1-7) | 5% |
| 3-HH-V | (2-1) | 33% |
| V2-BB-1 | (2-3) | 6% |
| 3-HHB-1 | (2-5) | 5% |
| 5-HBBH-3 | (2-11) | 3% |
| 3-HBB(F,F)-F | (3-8) | 3% |
| 5-HBB(F,F)-F | (3-8) | 4% |
| 3-GB(F,F)XB(F,F)-F | (3-12) | 9% |
| 3-BB(F)B(F,F)-CF3 | (3-14) | 4% |
| 3-HBBXB(F,F)-F | (3-20) | 5% |
| 5-HBBXB(F,F)-F | (3-20) | 4% |
| 4-GB(F)B(F,F)XB(F,F)-F | (3-23) | 5% |
| 4-BB(F)B(F,F)XB(F,F)-F | (3-25) | 6% |

NI=72.4° C.; Tc<−30° C.; Δn=0.113; Δε=13.1; Vth=1.35 V; η=13.4 mPa·s.

Example 9

| | | |
|---|---|---|
| 3-BB(F,F)XB(F)B(F,F)-F | (1-3) | 5% |
| 4-BB(F,F)XB(F)B(F,F)-F | (1-3) | 3% |
| 3-BB(F,F)XB(F)B(F)-F | (1-6) | 3% |
| 3-HH-V | (2-1) | 34% |
| 1V2-BB-1 | (2-3) | 4% |
| 3-HHEH-3 | (2-4) | 3% |
| 3-HHEBH-3 | (2-10) | 3% |
| 3-HHEBH-5 | (2-10) | 3% |
| 5-HB(F)BH-3 | (2-12) | 3% |
| 3-HGB(F,F)-F | (3-6) | 4% |
| 5-GHB(F,F)-F | (3-7) | 4% |
| 3-HBB(F,F)-F | (3-8) | 3% |
| 3-BBXB(F,F)-F | (3-15) | 7% |
| 3-BB(F,F)XB(F,F)-F | (3-16) | 6% |
| 3-HBB(F,F)XB(F,F)-F | (3-21) | 5% |
| 4-BB(F)B(F,F)XB(F,F)-F | (3-25) | 3% |
| 5-BB(F)B(F,F)XB(F)B(F,F)-F | (3-26) | 3% |
| 1O1-HBBH-5 | (—) | 4% |

NI=78.3° C.; Tc<−30° C.; Δn=0.108; Δε=10.2; Vth=1.46 V; η=11.8 mPa·s.

Example 10

| | | |
|---|---|---|
| 3-BB(F,F)XB(F)B(F)-OCF3 | (1-4) | 3% |
| 3-BB(F,F)XB(F)B(F)-F | (1-6) | 5% |
| 4-B(F)B(F,F)XB(F,F)B(F,F)-F | (1-10) | 3% |
| 2-HH-3 | (2-1) | 10% |
| 5-HH-V | (2-1) | 15% |
| 3-HH-V1 | (2-1) | 6% |
| 1V2-HH-3 | (2-1) | 4% |
| V-HHB-1 | (2-5) | 10% |
| 1-BB(F)B-2V | (2-8) | 4% |
| 3-BB(F)B-2V | (2-8) | 5% |
| 3-HB(F)HH-2 | (2-9) | 3% |
| 3-HHEBH-4 | (2-10) | 3% |
| 5-HB-CL | (3-1) | 4% |
| 4-HHEB(F,F)-F | (3-4) | 3% |
| 3-BBXB(F,F)-F | (3-15) | 4% |
| 3-dhBB(F,F)XB(F,F)-F | (3-22) | 3% |
| 3-GB(F)B(F,F)XB(F,F)-F | (3-23) | 3% |
| 4-GB(F)B(F,F)XB(F,F)-F | (3-23) | 5% |
| 4-BB(F)B(F,F)XB(F)-F | (3-24) | 4% |
| 1O1-HBBH-3 | (—) | 3% |

NI=91.7° C.; Tc<−30° C.; Δn=0.118; Δε=9.2; Vth=1.48 V; η=11.1 mPa·s.

Example 11

| | | |
|---|---|---|
| 5-BB(F,F)XB(F)B(F,F)-F | (1-3) | 3% |
| 3-BB(F,F)XB(F)B(F,F)-CF3 | (1-5) | 3% |
| 4-B(F)B(F,F)XB(F)B(F,F)-F | (1-7) | 3% |
| 6-B(F)B(F,F)XB(F,F)B(F,F)-F | (1-10) | 3% |
| 3-HH-V | (2-1) | 33% |
| 4-HH-V1 | (2-1) | 5% |
| 7-HB-1 | (2-2) | 3% |
| V2-HHB-1 | (2-5) | 7% |
| 5-HBB(F)B-2 | (2-13) | 4% |
| 3-HHB(F,F)-F | (3-3) | 3% |
| 3-HB(F)B(F,F)-F | (3-9) | 3% |
| 3-GB(F)B(F,F)-F | (3-11) | 3% |
| 3-BBXB(F,F)-F | (3-15) | 5% |
| 4-HHB(F)B(F,F)-F | (3-18) | 5% |
| 3-HBB(F,F)XB(F,F)-F | (3-21) | 3% |
| 5-HBB(F,F)XB(F,F)-F | (3-21) | 7% |
| 4-BB(F)B(F,F)XB(F,F)-F | (3-25) | 7% |

NI=82.7° C.; Tc<−30° C.; Δn=0.111; Δε=11.1; Vth=1.34 V; η=12.5 mPa·s.

The compositions in Example 1 to Example 11 had a larger dielectric anisotropy and a lower minimum temperature in comparison with the composition in Comparative Example 1. Therefore, the liquid crystal composition of the invention is concluded to have excellent characteristics.

INDUSTRIAL APPLICABILITY

A liquid crystal composition of the invention satisfies at least one of characteristics such as a high maximum temperature, a low minimum temperature, a small viscosity, a suitable optical anisotropy, a large dielectric anisotropy, a large specific resistance, a high stability to ultraviolet light, a high stability to heat and a large elastic constant, or has a suitable balance regarding at least two of the characteristics. A liquid crystal display device including the composition has a short response time, a large voltage holding ratio, a large contrast ratio, a long service life and so forth, and thus can be used for a liquid crystal projector, a liquid crystal television and so forth.

What is claimed is:
1. A liquid crystal composition that has a nematic phase and contains at least one compound selected from compounds represented by formula (1) as a first component and at least one compound selected from compounds represented by formula (3), wherein a ratio of the first component is in a range of 10% by weight to 30% by weight based on a weight of the liquid crystal composition, and at least one compound in the at least one compound selected from compounds represented by formula (3) is selected from compounds represented by formulae (3-11), (3-14) and (3-19),

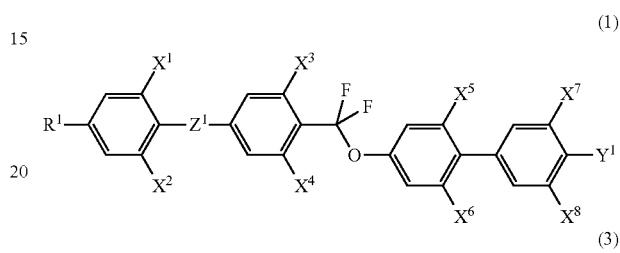

(1)

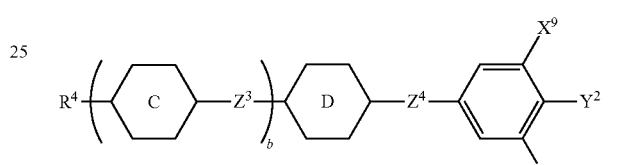

(3)

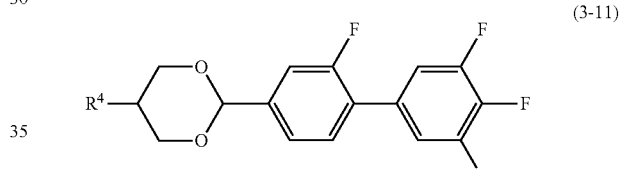

(3-11)

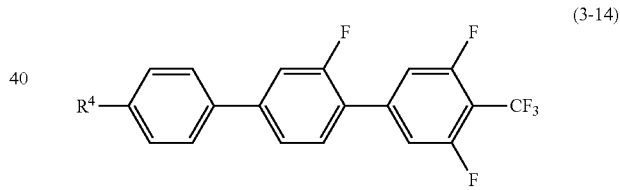

(3-14)

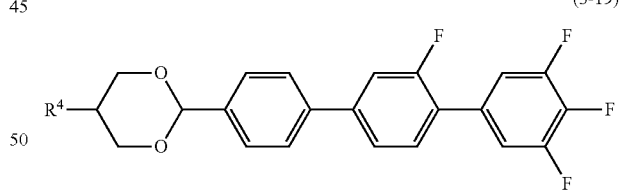

(3-19)

wherein in formula (1), $R^1$ is alkyl having 1 to 12 carbons, alkoxy having 1 to 12 carbons or alkenyl having 2 to 12 carbons; $Z^1$ is a single bond, ethylene or carbonyloxy; $X^1$, $X^2$, $X^3$, $X^4$, $X^5$, $X^6$, $X^7$ and $X^8$ are independently hydrogen or fluorine; and $Y^1$ is fluorine, chlorine, alkyl having 1 to 12 carbons in which at least one of hydrogen is replaced by halogen, or alkoxy having 1 to 12 carbons in which at least one of hydrogen is replaced by halogen, in formula (3), $R^4$ is alkyl having 1 to 12 carbons, alkoxy having 1 to 12 carbons or alkenyl having 2 to 12 carbons; ring C and ring D are independently 1,4-cyclohexylene, 1,4-phenylene, 2-fluoro-1,4-phenylene, 2,6-difluoro-1,4-phenylene, pyrimidine-2,5-diyl, 1,3-dioxane-2,5-diyl or tetrahydropyran- 2,5-diyl; $Z^3$ and $Z^4$ are independently a single bond, ethylene, carbonyloxy or difluoromethyleneoxy; $X^9$ and $X^{10}$ are independently hydrogen or fluorine; $Y^2$ is fluorine, chlorine, alkyl having 1 to 12 carbons in which at least one of hydrogen is replaced by halogen, or alkoxy having 1 to 12 carbons in which at least one of hydrogen is replaced by halogen; b is 0, 1, 2 or 3; and when b is 2, $Z^3$ is a single bond, ethylene or carbonyloxy, and in formulae (3-11), (3-14) and (3-19), $R^4$ is alkyl having 1 to 12 carbons, alkoxy having 1 to 12 carbons or alkenyl having 2 to 12 carbons.

2. The liquid crystal composition according to claim 1, containing at least one compound selected from the group of compounds represented by formula (1-1) to formula (1-10) as the first component:

(1-1)
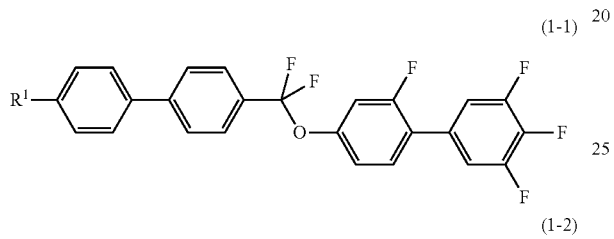

(1-2)
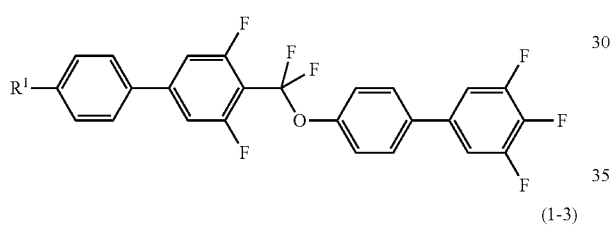

(1-3)
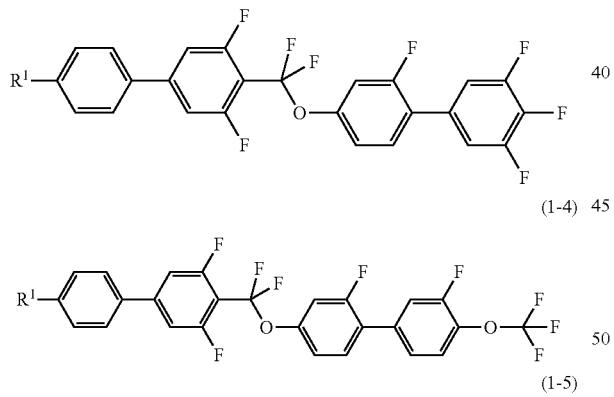

(1-4)
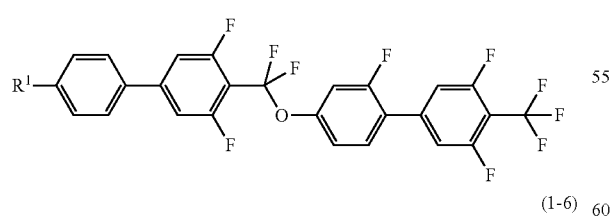

(1-5)
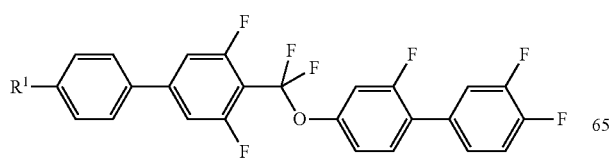

(1-6)

(1-7)
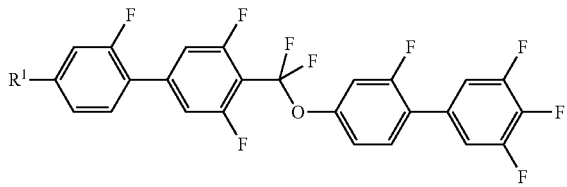

(1-8)
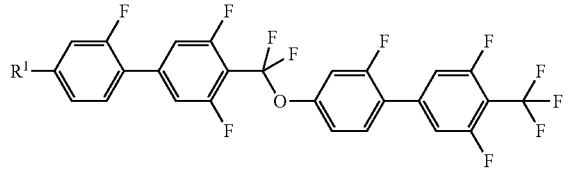

(1-9)
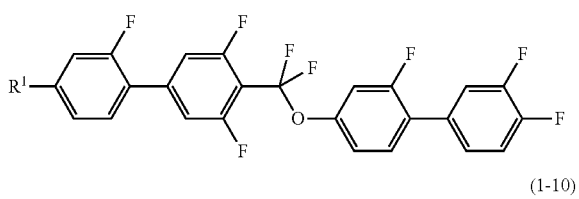

(1-10)
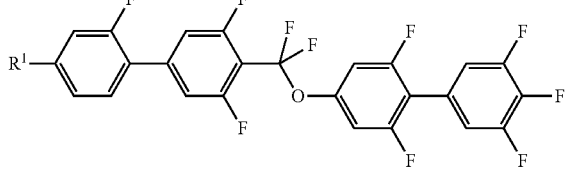

wherein, $R^1$ is alkyl having 1 to 12 carbons, alkoxy having 1 to 12 carbons or alkenyl having 2 to 12 carbons.

3. The liquid crystal composition according to claim 1, further containing at least one compound selected from compounds represented by formula (2) as a second component:

(2)
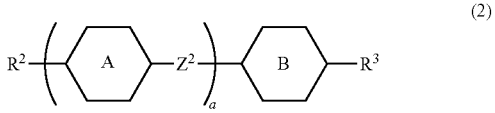

wherein, in formula (2), $R^2$ and $R^3$ are independently alkyl having 1 to 12 carbons, alkoxy having 1 to 12 carbons, alkenyl having 2 to 12 carbons, alkyl having 1 to 12 carbons in which at least one of hydrogen is replaced by fluorine, or alkenyl having 2 to 12 carbons in which at least one of hydrogen is replaced by fluorine; ring A and ring B are independently 1,4-cyclohexylene, 1,4-phenylene, 2-fluoro-1,4-phenylene or 2,5-difluoro-1,4-phenylene; $Z^2$ is a single bond, ethylene or carbonyloxy; and a is 1, 2 or 3.

4. The liquid crystal composition according to claim 3, containing at least one compound selected from the group of compounds represented by formula (2-1) to formula (2-13) as the second component:

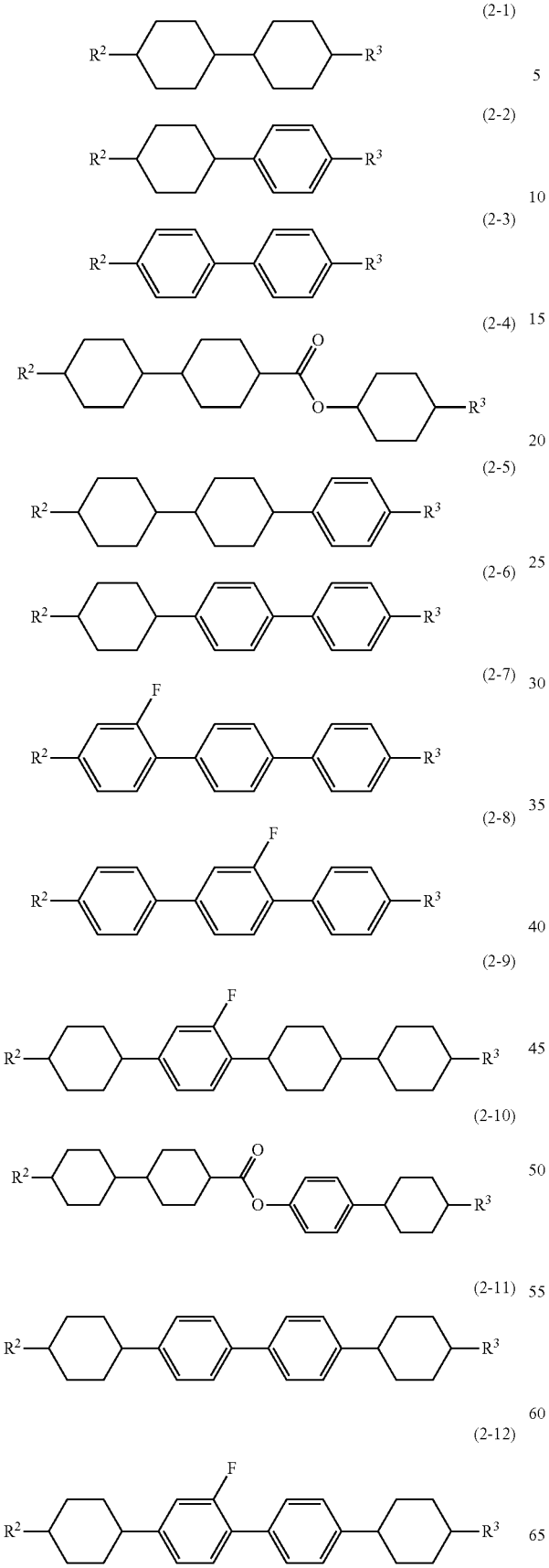

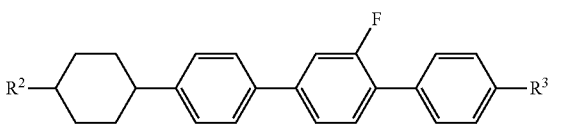

wherein, in formula (2-1) to formula (2-13), $R^2$ and $R^3$ are independently alkyl having 1 to 12 carbons, alkoxy having 1 to 12 carbons, alkenyl having 2 to 12 carbons, alkyl having 1 to 12 carbons in which at least one of hydrogen is replaced by fluorine, or alkenyl having 2 to 12 carbons in which at least one of hydrogen is replaced by fluorine.

5. The liquid crystal composition according to claim 3, wherein a ratio of the second component is in the range of 10% by weight to 90% by weight based on the weight of the liquid crystal composition.

6. The liquid crystal composition according to claim 1, wherein the at least one compound selected from compounds represented by formula (3) further contains at least one compound selected from the group of compounds represented by formulae (3-1) to (3-10), (3-12), (3-13), (3-15) to (3-18) and (3-20) to (3-26):

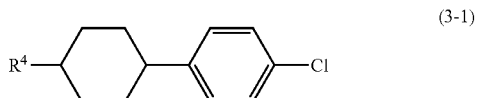

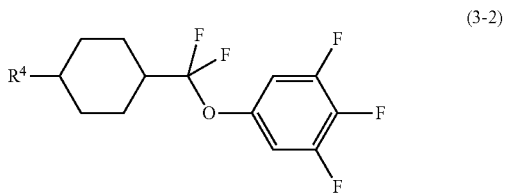

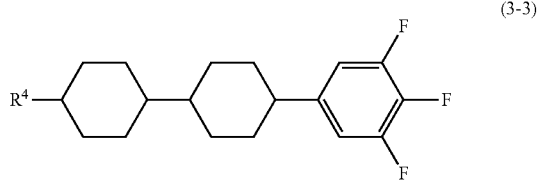

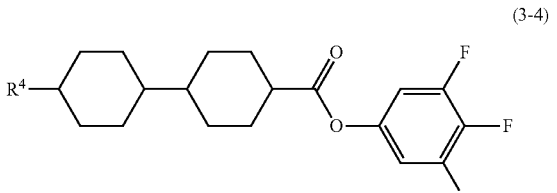

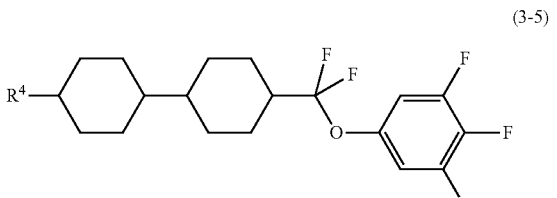

(3-6) 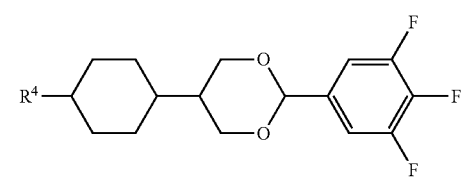
(3-7) 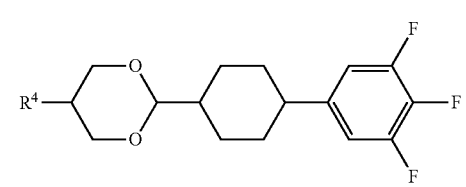
(3-8) 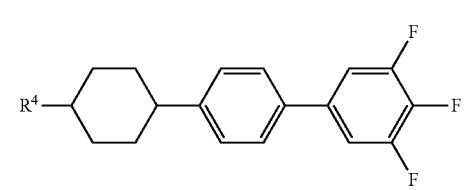
(3-9) 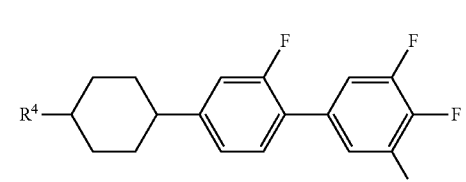
(3-10) 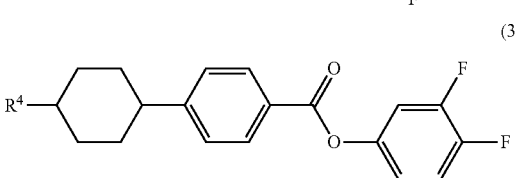
(3-11) 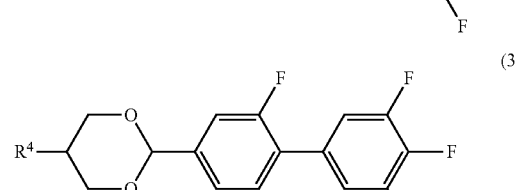
(3-12) 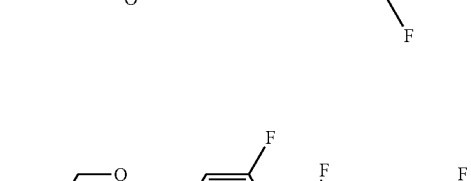
(3-13) 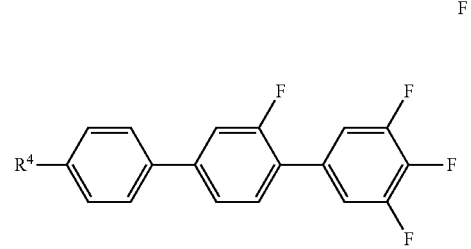
(3-14) 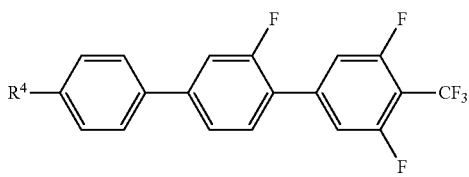
(3-15) 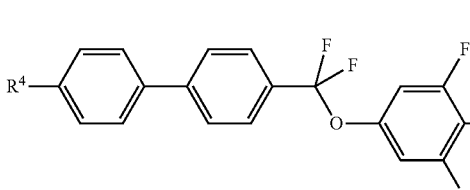
(3-16) 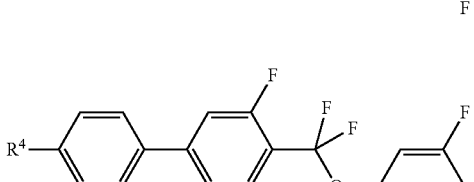
(3-17) 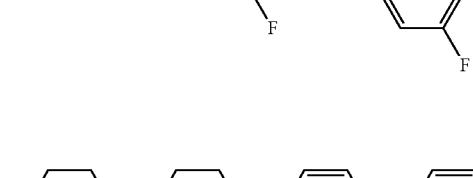
(3-18) 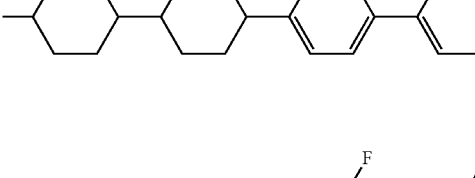
(3-19) 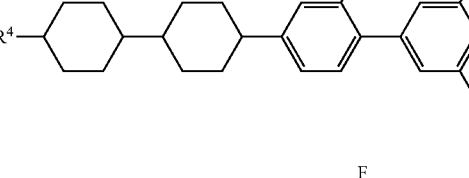
(3-20) 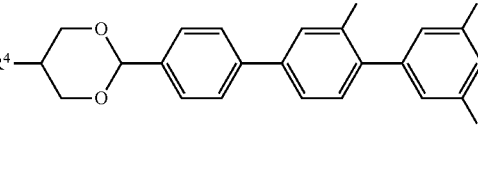
(3-21) 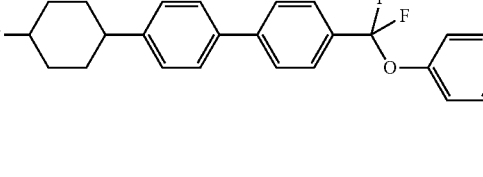

-continued (3-22)
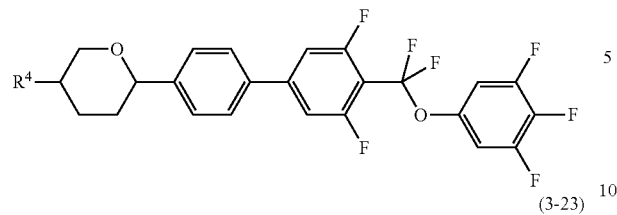

(3-23)
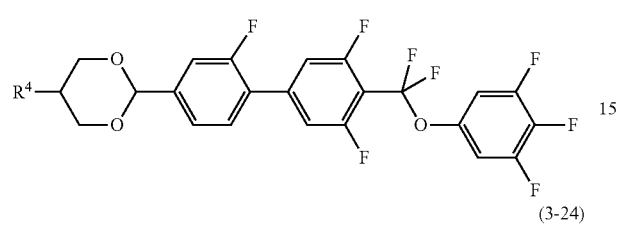

(3-24)
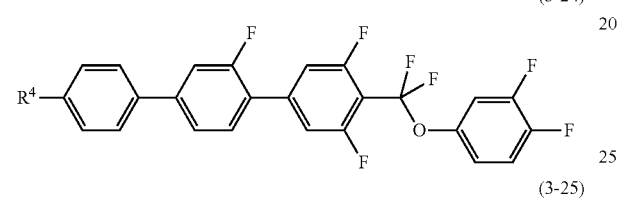

(3-25)
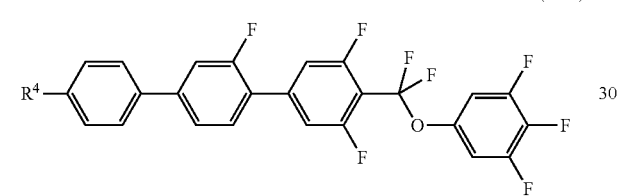

(3-26)

wherein, in formulae (3-1) to (3-10), (3-12), (3-13), (3-15) to (3-18) and (3-20) to (3-26), $R^4$ is alkyl having 1 to 12 carbons, alkoxy having 1 to 12 carbons or alkenyl having 2 to 12 carbons.

7. The liquid crystal composition according to claim 1, wherein a ratio of the at least one compound selected from compounds represented by formula (3) is in the range of 10% by weight to 90% by weight based on the weight of the liquid crystal composition.

8. The liquid crystal composition according to claim 1, wherein a maximum temperature of a nematic phase is 70° C. or higher, an optical anisotropy (measured at 25° C.) at a wavelength of 589 nanometers is 0.07 or more, and a dielectric anisotropy (measured at 25° C.) at a frequency of 1 kHz is 2 or more.

9. A liquid crystal display device, including the liquid crystal composition according to claim 1.

10. The liquid crystal display device according to claim 9, wherein an operating mode in the liquid crystal display device is a TN mode, an ECB mode, an OCB mode, an IPS mode or an FPA mode, and a driving mode in the liquid crystal display device is an active matrix mode.

* * * * *